United States Patent
Sarraf et al.

(10) Patent No.: US 12,391,659 B2
(45) Date of Patent: Aug. 19, 2025

(54) BENZOTHIAZOLE AND RELATED COMPOUNDS

(71) Applicant: Spinogenix, Inc., San Diego, CA (US)

(72) Inventors: Stella Sarraf, Beverly Hills, CA (US); Vincent F. Simmon, San Diego, CA (US); Gerald F. Swiss, San Diego, CA (US)

(73) Assignee: Spinogenix, Inc., Los Angeles, CA (US)

( * ) Notice: Subject to any disclaimer, the term of this patent is extended or adjusted under 35 U.S.C. 154(b) by 989 days.

(21) Appl. No.: 17/392,036

(22) Filed: Aug. 2, 2021

(65) Prior Publication Data

US 2022/0017477 A1 Jan. 20, 2022

Related U.S. Application Data

(63) Continuation of application No. 16/635,872, filed as application No. PCT/US2018/044852 on Aug. 1, 2018, now Pat. No. 11,117,878.

(60) Provisional application No. 62/540,311, filed on Aug. 2, 2017.

(51) Int. Cl.
C07D 277/66 (2006.01)
A61P 25/28 (2006.01)

(52) U.S. Cl.
CPC ............ C07D 277/66 (2013.01); A61P 25/28 (2018.01)

(58) Field of Classification Search
CPC ..... C07D 277/66; A61P 25/28; A61K 31/426; A61K 45/06
See application file for complete search history.

(56) References Cited

U.S. PATENT DOCUMENTS

| | | | |
|---|---|---|---|
| 7,666,886 B2 | 2/2010 | Yang et al. | |
| 8,741,883 B2 | 6/2014 | Yang et al. | |
| 10,675,273 B2 | 6/2020 | Yang | |
| 2009/0028787 A1 | 1/2009 | Gravenfors et al. | |
| 2014/0080843 A1 | 3/2014 | Huang et al. | |
| 2015/0299191 A1 | 10/2015 | Huang et al. | |

FOREIGN PATENT DOCUMENTS

| | | |
|---|---|---|
| WO | WO 2014/134287 | 9/2014 |
| WO | WO 2017/120198 | 7/2017 |
| WO | WO 2019/005682 | 1/2019 |
| WO | WO 2020/046991 | 3/2020 |
| WO | WO 2020/160332 | 8/2020 |

OTHER PUBLICATIONS

Wu et al. Triethylene glycol-modified iridium (III) complexes for fluorescence imaging of Schistosoma japonicum J. Mater. Chem. B, 5, 4973-4980. (Year: 2017).*
Wu et al. Triethylene glycol-modified iridium(III) complexes for fluorescence imagine of Schistosoma japonicum, J. Mater. Chem. B, 2017, 5, 4973-4980: Published May 18, 2017. (Year: 2017).*
Wu et al. supplemental. (Year: 2017).*
Ciapetti, et al. Molecular Variations Based on Isosteric Replacements. The Practice of Medicinal Chemistry. Elsevier, Amsterdam, NL. Jan. 1, 2008; Chapter 8: pp. 181-241.
Cifelli, et al. Benzothiazole Amphiphiles Ameliorate Amyloid β-Related Cell Toxicity and Oxidative Stress. ACS Chem. Neurosci. 2016, 7, 6, 682-688.
Cifelli, et al. Benzothiazole Amphiphiles Promote the Formation of Dendritic of dendritic spines in primary hippocampal neurons. Journal of Biological Chemistry. Jun. 3, 2016; 291(23):11981-11992.
Extended European Search Report and Search Opinion dated Mar. 31, 2021 for EP Application No. 18840208.5. 12 pages.
Habib, L.K. et al. (Dec. 10, 2010, e-published Oct. 5, 2010). "Inhibitors of catalase-amyloid interactions protect cells from beta-amyloid-induced oxidative stress and toxicity," J Biol Chem 285(50):38933-38943.
Huang, et al. Inhibition of cholinesterase activity and amyloid aggregation by berberine-phenyl-benzoheterocyclic and tacrine-phenylbenzoheterocyclic hybrids. Bioorganic & Medicinal Chemistry. May 1, 2012; 20(3):3038-3048.
Inbar, P. et al. (Oct. 2006). "Oligo(ethylene glycol) derivatives of thioflavin T as inhibitors of protein-amyloid interactions," ChemBioChem 7(10):1563-1566.
International Search Report and Written Opinioned dated Mar. 30, 2017 for PCT Application No. PCT/US2017/012139, 12 pages.
International Search Report and Written Opinioned dated Sep. 12, 2018 for PCT Application No. PCT/ US2018/044852, 9 pages.
Lee, N.J. et al. (Feb. 2016, e-published Dec. 8, 2015). "Hexa (ethylene glycol) derivative of benzothiazole aniline promotes dendritic spine formation through the RasGRF1-Ras dependent pathway," Biochim Biophys Acta 1862(2):284-295.
Megill, A. et al. (May 29, 2013). "A tetra(ethylene glycol) derivative of benzothiazole aniline enhances Ras-mediated spinogenesis," J Neurosci 33(22):9306-9318.
Prangkio, P. et al. (Dec. 2011, e-published Aug. 26, 2011). "Self-assembled, cation-selective ion channels from an oligo(ethylene glycol) derivative of benzothiazole aniline," Biochim Biophys Acta 1808(12):2877-2885.
Prangkio, P. et al. (2012, e-published Oct. 15, 2012). "Multivariate analyses of amyloid-beta oligomer populations indicate a connection between pore formation and cytotoxicity," PLoS One 7(1O):e47261.
Song, J.M. et al. (Feb. 2014, e-published Dec. 6, 2013). "A tetra(ethylene glycol) derivative of benzothiazole aniline ameliorates dendritic spine density and cognitive function in a mouse model of Alzheimer's disease," Exp Neural 252:105-113.
Supplementary European Search Report and Search Opinion dated Jul. 19, 2019 for EP Application No. 17736233.2. 7 pages.
Wu, et al. Triethylene glycol-modified iridium(iii) complexes for fluorescence imaging of Schistosoma japonicum. Journal of Materials Chemistry. Jan. 1, 2017; 5(25):4973-4980.

(Continued)

Primary Examiner — Joseph K McKane
Assistant Examiner — Meghan C Heasley
(74) Attorney, Agent, or Firm — Sheppard Mullin Richter & Hampton LLP

(57) ABSTRACT

Disclosed are compounds that promote spinogenesis, are capable of reducing the neural toxicity of beta-amyloid peptides, and/or reduce the symptoms of traumatic brain injury in a patient.

18 Claims, 9 Drawing Sheets

(56) References Cited

OTHER PUBLICATIONS

Wu, et al. Supporting Information—Triethylene glycol-modified iridium(iii) complexes for fluorescence imaging of Schistosoma japonicum. Journal of Materials Chemistry. Jan. 1, 2017; pp. 1-3.
Yang, J. et al. (Jul. 26, 2002). "Catalytic oxidations of steroid substrates by artificial cytochrome p-450 enzymes," J Org Chem 67(15):5057-5067.
Zhao, X. et al. (Oct. 20, 2010). "Amyloid-β peptide is a substrate of the human 20S proteasome," ACS Chem Neurosci 1(10):655-660.
Masakatsu Nozaki, et al. Soyaku Kagaku [Drug development chemistry], Kagaku Dojin, Jul. 1, 1995, p. 98-99.

* cited by examiner

"Benzothiazole-I"

((4-(6-methylbenzo[d]thiazol-2-yl)phenyl)amino)-
$(CH_2CH_2O)_4H$

"Benzothiazole-II"

((4-(benzo[d]thiazol-2-yl)phenyl)thio)-
$(CH_2CH_2O)_6H$

"Benzothiazole-IIIA"

((4-(benzo[d]thiazol-2-yl)phenoxy)-$(CH_2CH_2O)_6H$

"Benzothiazole-IIIB"

((4-(benzo[d]thiazol-2-yl)phenoxy)-$(CH_2CH_2O)_4H$

BENZOTHIAZOLE AND RELATED COMPOUNDS

CROSS-REFERENCES TO RELATED APPLICATIONS

The present application is a continuation of U.S. patent application Ser. No. 16/635,872, filed on Jan. 31, 2020, now issued as U.S. Pat. No. 11,117,878, which is a U.S. National Stage Application under 35 U.S.C. § 371 of International Application No. PCT/US2018/044852, filed on Aug. 1, 2018, which claims priority to U.S. Provisional Application No. 62/540,311, filed on Aug. 2, 2017, the entire contents of all of which are hereby incorporated by reference in their entirety.

BACKGROUND OF THE INVENTION

Dendritic complexity, synaptogenesis, and overall proper development and function of neurons are critical for proper functioning of the brain. Traumatic brain injuries (TBI) lead to memory loss and production of beta amyloid peptides, which have been linked to Alzheimer's disease. One long term consequence of TBIs is the reduced dendritic spine density in key areas of the brain. This invention provides for compounds that promote spinogenesis and/or are capable of reducing the neural toxicity of beta-amyloid peptides.

SUMMARY OF THE INVENTION

In one embodiment, the invention provides a compound according to Formula I and/or Formula IA:

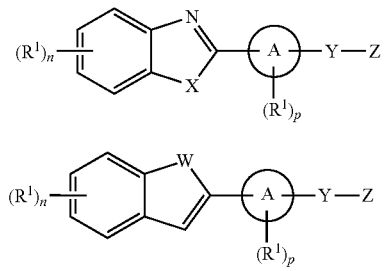

or a pharmaceutically acceptable salt, solvate, and/or an N-oxide thereof, wherein subscripts n and p are independently selected from 0, 1 or 2;
each $R^1$ is independently selected from the group consisting of halo, alkyl, substituted alkyl, alkoxy, substituted alkoxy, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, thiol, and nitro;
A is an arylene or heteroarylene, having 1 to 4 heteroatoms;
W is selected from the group consisting of —O—, —S—, —SO—, —S(O)$_2$—, and —NR$^{12}$—, wherein R$^{12}$ is selected from the group consisting of hydrogen, alkyl, substituted alkyl, aryl, substituted aryl, heteroaryl, substituted heteroaryl, heterocycloalkyl, and substituted heterocycloalkyl;
X is selected from the group consisting of —O—, —S—, —SO—, —S(O)$_2$—, and —NR$^{12}$—, wherein R$^{12}$ is as defined above, provided that when A is arylene, and Y is —S— or —NR$^{12}$—, then X is not —S—;
Y is selected from the group consisting of —O—, —S—, —SO—, S(O)$_2$—, and —NR$^{12}$—, wherein R$^{12}$ is as defined above; and
Z is selected from the group consisting of —N(CH$_3$)$_2$ CH$_2$CH$_2$OC(O)CH$_3$ and —(CH$_2$CH(R$^{13}$)O)$_q$-T, wherein subscript q is an integer selected from 1 to 100, R$^{13}$ is selected from the group consisting of hydrogen and methyl, and T is selected from the group consisting of hydrogen, alkyl, substituted alkyl, -L-monosaccharide, and -L-oligosaccharide, wherein L is selected from the group consisting of a bond, phosphate, and sulfate.

In one embodiment, the invention provides a compound according to Formula II, Formula III, Formula IV, Formula V, and/or Formula VI:

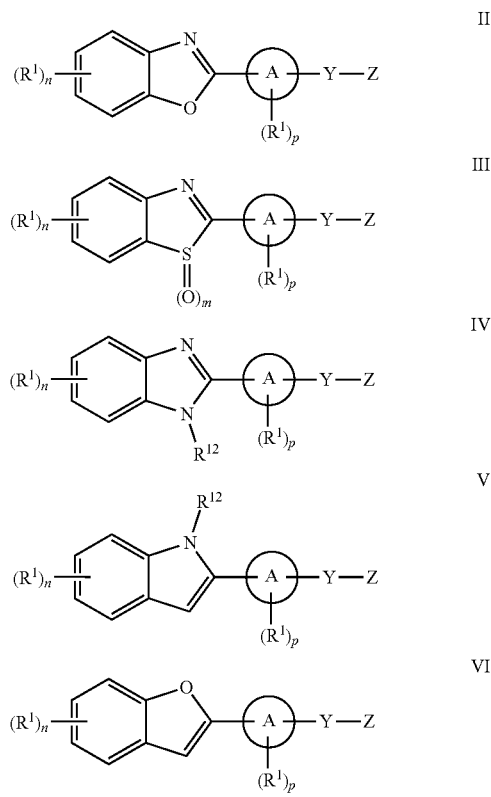

or a pharmaceutically acceptable salt, solvate, and/or an N-oxide thereof, wherein
R$^1$, R$^{12}$, A, Y, Z, n and p are as defined above; and
subscript m is selected from 0, 1 or 2.

In one embodiment, Y is selected from the group consisting of —O—, —S—, and —NR$^{12}$—, wherein R$^{12}$ is as defined above.

In one embodiment, T is hydrogen.

In one embodiment, the invention provides a compound as described herein, or a pharmaceutically acceptable salt, solvate, and/or an N-oxide thereof, selected from:

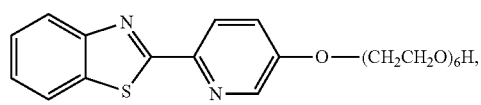

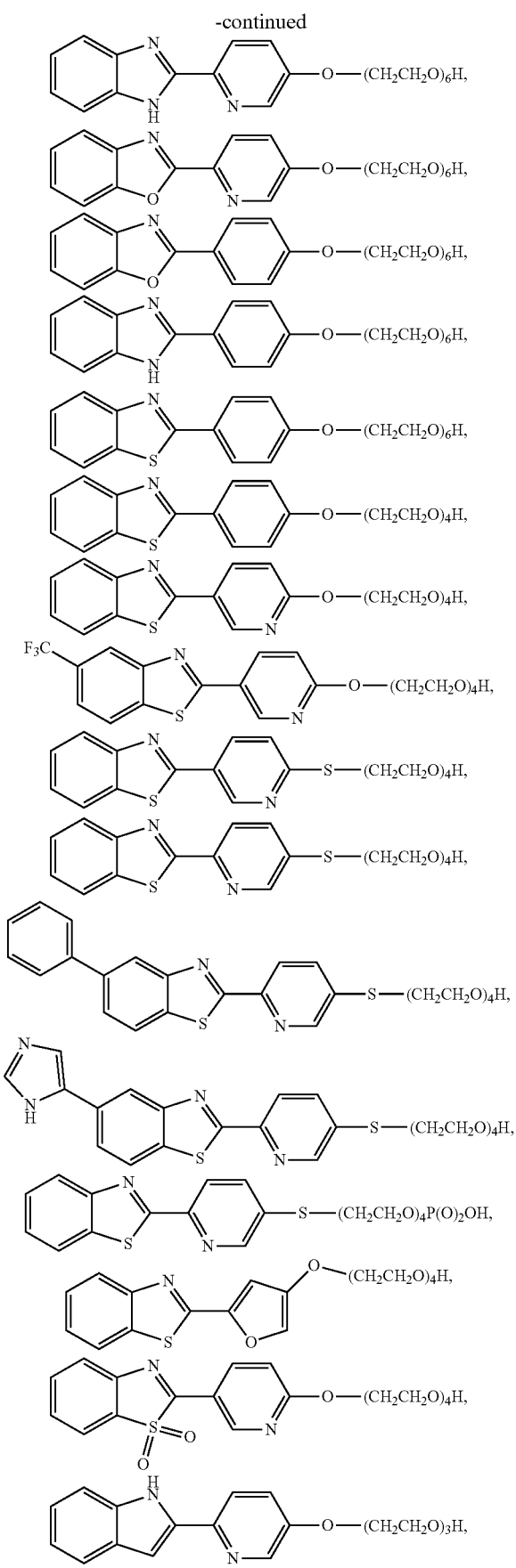

In one embodiment, the invention provides a compound according to Formula VII:

(VII)

$(R^1)_n$ —[benzothiazole]— [phenyl($R^2)_p$]— O—(CH$_2$CH$_2$O)$_q$—H, or a pharmaceutically acceptable salt or solvate thereof, wherein:
subscripts n and p are independently selected from 0, 1 or 2;
subscript q is an integer selected from 2 to 8; and
each $R^1$ and $R^2$ are independently selected from the group consisting of halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro.

In one embodiment, subscript q is an integer selected from 3 to 6; $R^1$ is selected from the group consisting of halo, —OH, —CN, phenyl, —CHCH$_2$, —COCH$_3$, —COOCH$_3$, —CH$_2$SO$_2$NH$_2$, —NHCOCH$_3$, —N(CH$_3$)$_2$, —SCH$_3$, and —SO$_2$NH$_2$; and $R^2$ is selected from the group consisting of halo, —CH$_3$, —CH$_2$CH$_3$, cyclopentyl, —CF$_3$, —CN, —CHCH$_2$, —CH$_2$CHCH$_2$, phenyl, —CO$_2$H, —CH$_2$CO$_2$H, —CH$_2$CONH$_2$, —COOCH$_3$, —COCH$_3$, —(CH$_2$)$_2$OCH$_3$, —CONH$_2$, —CON(CH$_3$)$_2$, —CH$_2$SO$_2$N(CH$_3$)$_2$, —OCH$_3$, —OCF$_3$, —OCH(CH$_3$)$_2$, —N(CH$_3$)$_2$, —NHCOCH$_3$, —NO$_2$, —SCH$_3$, —SO$_2$CH$_3$, and —SO$_2$N(CH$_3$)$_2$.

In one embodiment, subscripts n and p are independently selected from 0 or 1, provided that subscripts n and p are not both 1.

In one embodiment, the invention provides a compound, or a pharmaceutically acceptable salt or solvate thereof, as described herein, selected from:

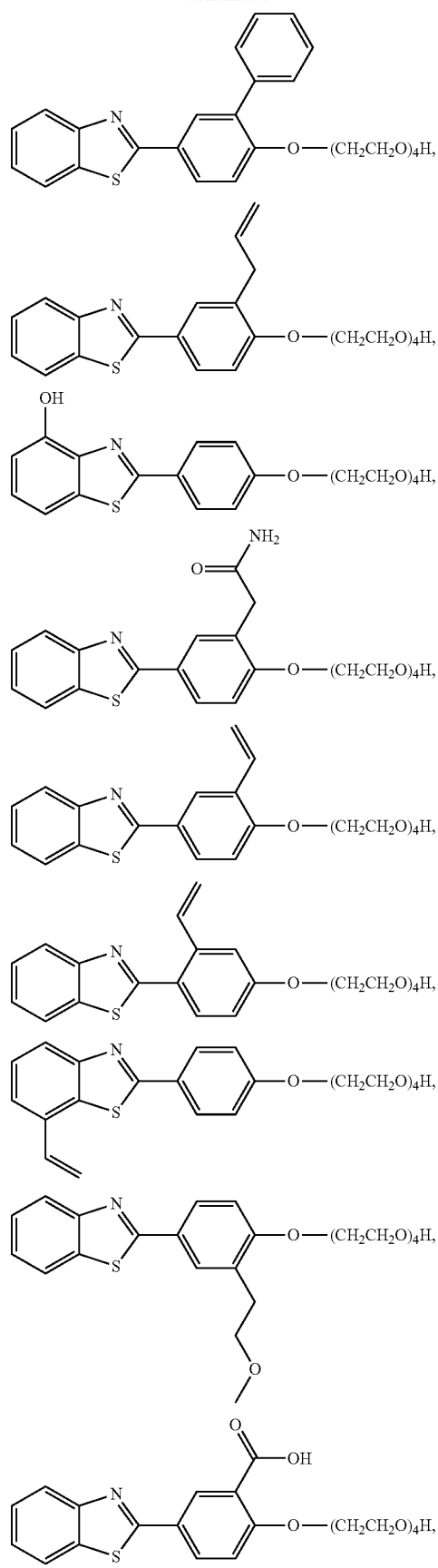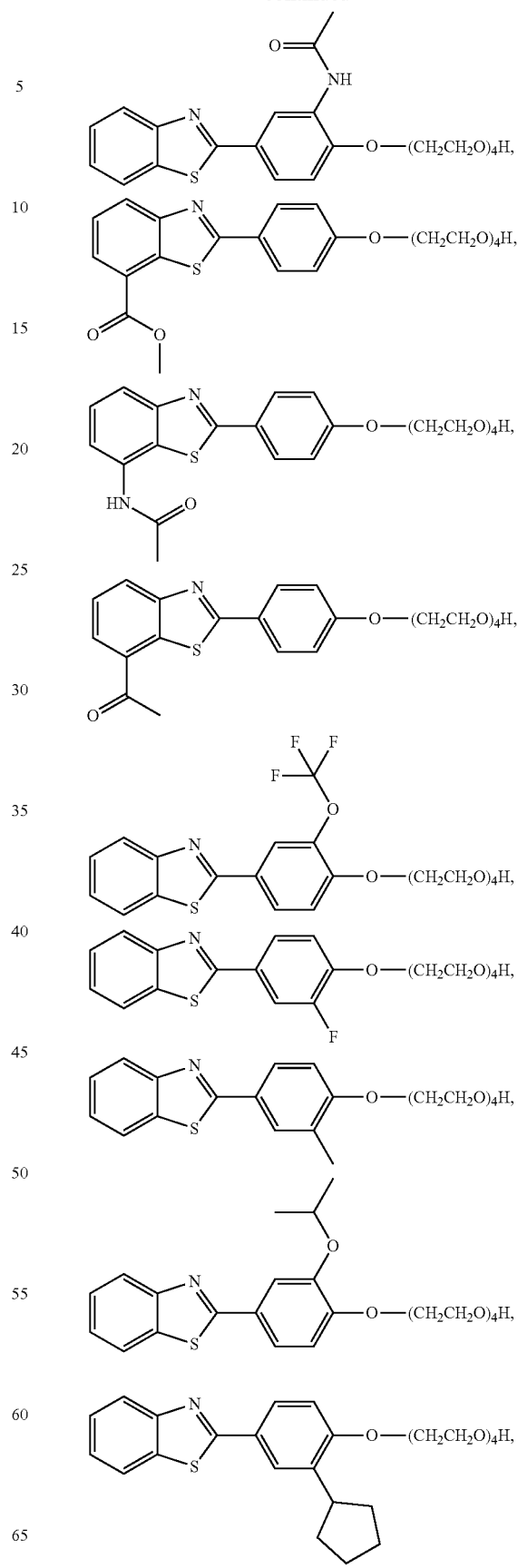

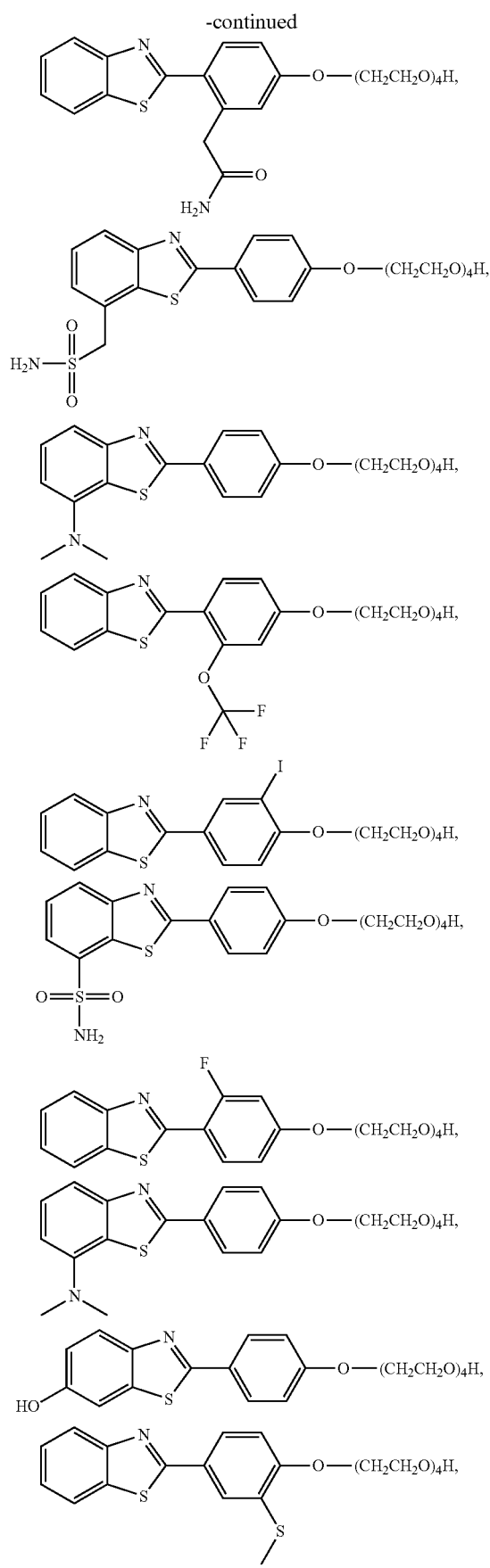
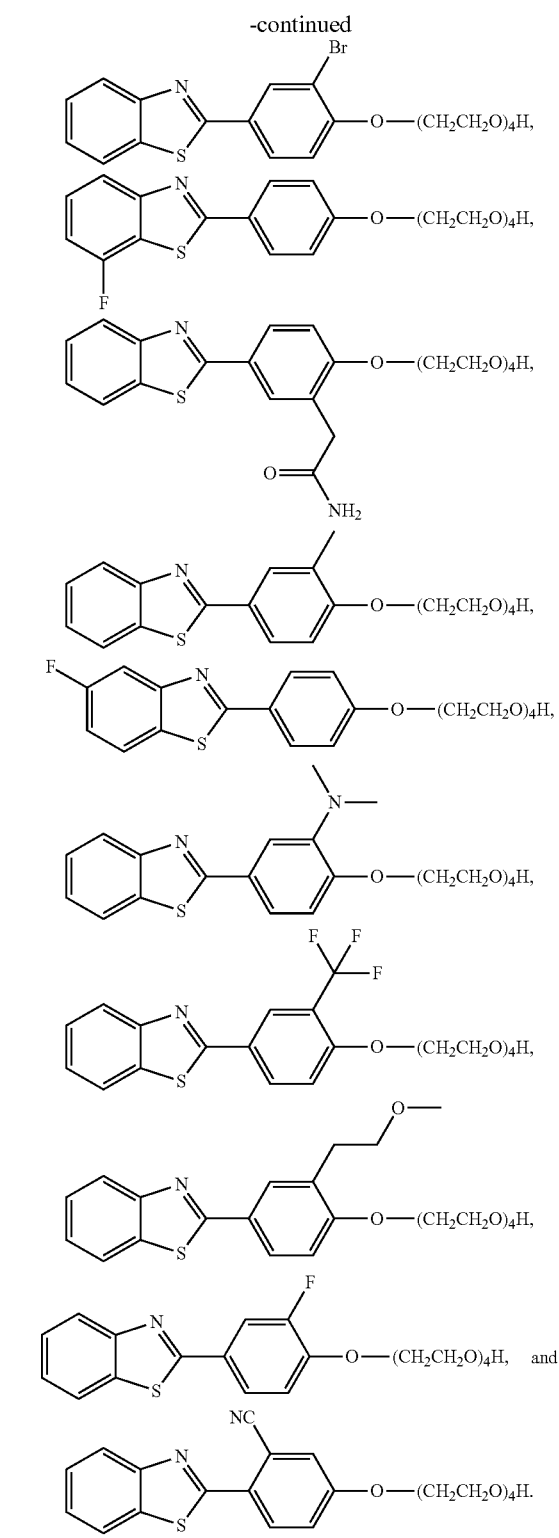
In one embodiment, $R^1$ is selected from the group consisting of halo, —$CH_3$, —$OCH_3$, phenyl, and —CN; and $R^2$ is selected from the group consisting of halo, —$CH_3$, —$CF_3$, —$OCH_3$, —$OCF_3$, —$CHCH_2$, —$CH_2CHCH_2$, phenyl, and —$NO_2$.
In one embodiment, the invention provides a compound according to Formula VIIa:

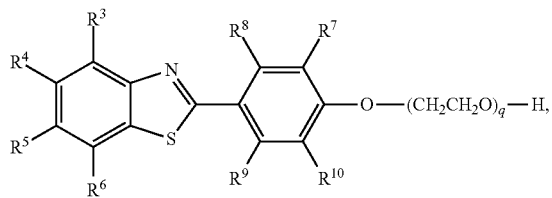

(VIIa)

or a pharmaceutically acceptable salt or solvate thereof, wherein:
subscript q is an integer selected from 4 or 6;
$R^3$, $R^4$, $R^5$, and $R^6$ are independently selected from the group consisting of hydrogen, halo, —$CH_3$, and —$OCH_3$; and
$R^7$, $R^8$, $R^9$ and $R^{19}$ are independently selected from the group consisting of hydrogen, halo, —$CH_3$, —$CF_3$, —$OCH_3$, —$OCF_3$, phenyl, —$NO_2$;
wherein at least six of said R groups are hydrogen.

In one embodiment, the invention provides a compound, or a pharmaceutically acceptable salt or solvate thereof, selected from:

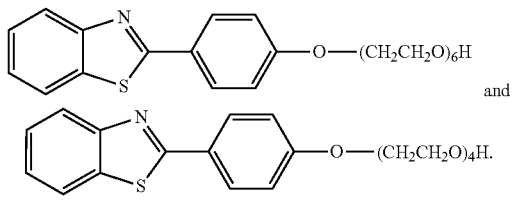

In one embodiment, the invention provides the following compound, or pharmaceutically acceptable salt or solvate thereof:

In one embodiment, the invention provides a pharmaceutical composition containing a therapeutically effective amount of a compound as described herein, or a pharmaceutically acceptable salt or solvate thereof, and one or more pharmaceutically acceptable excipients.

In one embodiment, the invention provides a method for increasing dendritic spine density of neurons. The method includes contacting the neurons with a therapeutically effective amount of a compound, or pharmaceutically acceptable salt or solvate thereof, or a composition as described herein under conditions sufficient to increase dendritic spine density of neurons.

In one embodiment, the method for increasing dendritic spine density of neurons is conducted subsequent to a traumatic brain injury.

In one embodiment, the invention provides a method for decreasing the neurotoxicity of beta-amyloid peptides to neurons. The method includes contacting the beta-amyloid peptides with a therapeutically effective amount of a compound, or pharmaceutically acceptable salt or solvate thereof, or a composition as described herein under conditions sufficient to decrease the neurotoxicity of the beta-amyloid peptides.

In one embodiment, the invention provides a method for reducing the symptoms of traumatic brain injury in a patient suffering from traumatic brain injury. The method of reducing the symptoms of traumatic brain injury in a patient includes administering a therapeutically effective amount of a compound, or pharmaceutically acceptable salt or solvate thereof, or pharmaceutical composition as described herein, wherein the therapeutically effective amount of the compound, or pharmaceutically acceptable salt or solvate thereof, is an amount sufficient to reduce the symptoms of traumatic brain injury.

In one embodiment, the method for reducing the symptoms of traumatic brain injury in a patient is conducted within about 0 to 72 hours of the traumatic brain injury.

In an aspect of the method for reducing the symptoms of traumatic brain injury in a patient, the reduction of the symptoms of trauma is measured by an improvement in the performance of one or more functional domains by at least 20% to 30% within about 7 days of treatment as compared to the performance of the one or more functional domains measured prior to treatment but after injury.

DETAILED DESCRIPTION

Figure 1:
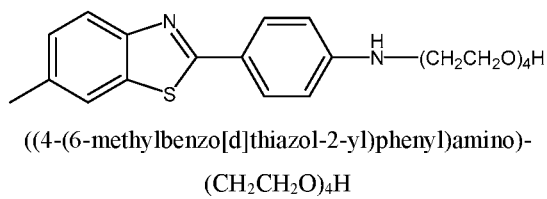
FIG. 1. Chemical structures of Benzothiazole-I (i.e., ((4-(6-methylbenzo[d]thiazol-2-yl)phenyl)amino)-($CH_2CH_2O)_4H$), Benzothiazole-II (i.e., ((4-(benzo[d]thiazol-2-yl)phenyl)thio)-($CH_2CH_2O)_6H$), Benzothiazole-IIIA (i.e., ((4-(benzo[d]thiazol-2-yl)phenoxy)-($CH_2CH_2O)_6H$), and Benzothiazole-IIIB (i.e., ((4-(benzo[d]thiazol-2-yl)phenoxy)-($CH_2CH_2O)_4H$), as indicated.
Figure 1:
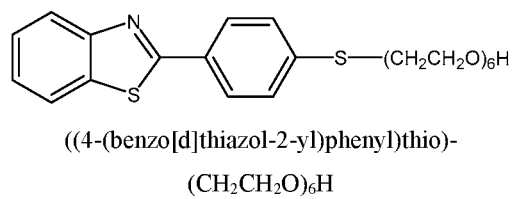
Figure 1:
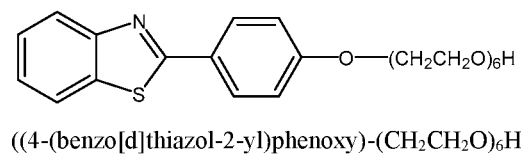
Figure 1:
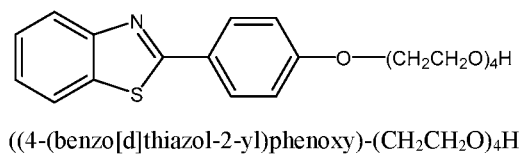

The present invention provides compounds and compositions for promoting spinogenesis. The compounds and compositions of the present invention are useful for increasing dendritic spine density of neurons, and are also useful for decreasing the neurotoxicity of beta-amyloid peptides to neurons.

I. DEFINITIONS

The abbreviations used herein have their conventional meaning within the chemical and biological arts.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$, and $S^{35}$ are thus within the scope of this invention. Procedures for inserting such labels into the compounds of this invention will be readily apparent to those skilled in the art based on the disclosure herein.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminocarbonylamino, aminocarbonyloxy, aminosulfonyl, aminosulfonyloxy, aminosulfonylamino, amidino, aryl, substituted aryl, aryloxy, substituted aryloxy, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkenyl, substituted cycloalkenyl, guanidino, halo, hydroxy, heteroaryl, substituted heteroaryl, heteroaryloxy, substituted heteroaryloxy, heterocyclic, substituted heterocyclic, heterocyclyloxy, substituted heterocyclyloxy nitro, —$SO_3H$, substituted sulfonyl, substituted sulfonyloxy, and thiol.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminocarbonylamino, aminocarbonyloxy, aminosulfonyl, aminosulfonyloxy, aminosulfonylamino, amidino, aryl, substituted aryl, aryloxy, substituted aryloxy, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkenyl, substituted cycloalkenyl, cycloalkenyloxy, substituted cycloalkenyloxy, guanidino, halo, hydroxyl, heteroaryl, substituted heteroaryl, heteroaryloxy, substituted heteroaryloxy, heterocyclic, substituted heterocyclic, heterocyclyloxy, substituted heterocyclyloxy, nitro, $SO_3H$, substituted sulfonyl, substituted sulfonyloxy and thiol and with the proviso that any hydroxyl or thiol substitution is not attached to a vinyl (unsaturated) carbon atom.

"Alkylene" refers to divalent saturated aliphatic hydrocarbyl groups having from 1 to 10 carbon atoms, preferably having from 1 to 6 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$— or —$CH(CH_3)CH_2$—), butylene (—$CH_2CH_2CH_2CH_2$—), isobutylene (—$CH_2CH(CH_3)CH_2$—), sec-butylene (—$CH(CH_3)CH_2CH_2$— or —$CH_2CH_2(CH_3)CH$—), and the like. Similarly, "alkenylene" refer to an alkylene moiety containing respective 1 or 2 carbon carbon double bonds.

"Substituted alkylene" refers to an alkylene group having from 1 to 3 hydrogen atoms replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy. "Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—. Acyl includes the "acetyl" group $CH_3C(O)$—.

"Acylamino" refers to the groups —$NR^{47}C(O)$alkyl, —$NR^{47}C(O)$ substituted alkyl, —$NR^{47}C(O)$cycloalkyl, —$NR^{47}C(O)$ substituted cycloalkyl, —$NR^{47}C(O)$cycloalkenyl, —$NR^{47}C(O)$ substituted cycloalkenyl, —$NR^{47}C(O)$alkenyl, —$NR^{47}C(O)$ substituted alkenyl, —$NR^{47}C(O)$aryl, —$NR^{47}C(O)$ substituted aryl, —$NR^{47}C(O)$heteroaryl, —$NR^{47}C(O)$ substituted heteroaryl, —$NR^{47}C(O)$heterocyclic, and —$NR^{47}C(O)$ substituted heterocyclic, wherein $R^{47}$ is hydrogen or alkyl.

"Acyloxy" refers to the groups alkyl-C(O)O—, substituted alkyl-C(O)O—, alkenyl-C(O)O—, substituted alkenyl-C(O)O, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O—.

"Amino" refers to the group —$NH_2$. "Substituted amino" refers to the group —$NR^{48}R^{49}$, wherein $R^{48}$ and $R^{49}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic, and wherein $R^{48}$ and $R^{49}$ are optionally joined, together with the nitrogen bound thereto to form a heterocyclic or substituted heterocyclic group, provided that $R^{48}$ and $R^{49}$ are both not hydrogen.

"Aminocarbonyl" refers to the group —$C(O)NR^{50}R^{51}$, wherein $R^{50}$ and $R^{51}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and wherein $R^{50}$ and $R^{51}$ are optionally joined together with the nitrogen bound thereto to form a heterocyclic or substituted heterocyclic group.

"Aminocarbonylamino" refers to the group —$NR^{47}C(O)NR^{50}R^{51}$, wherein $R^{47}$ is hydrogen or alkyl; $R^{50}$ and $R^{51}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic; and, wherein $R^{50}$ and $R^{51}$ are optionally joined together with the nitrogen bound thereto to form a heterocyclic or substituted heterocyclic group.

"Aminocarbonyloxy" refers to the group —O—C(O)$NR^{50}R^{51}$, wherein $R^{50}$ and $R^{51}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and wherein $R^{50}$ and $R^{51}$ are optionally joined together with the nitrogen bound thereto to form a heterocyclic or substituted heterocyclic group.

"Aminosulfonyl" refers to the group —$SO_2NR^{50}R^{51}$, wherein $R^{50}$ and $R^{51}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and wherein $R^{50}$ and $R^{51}$ are optionally joined together with the nitrogen bound thereto to form a heterocyclic or substituted heterocyclic group.

"Aminosulfonyloxy" refers to the group —O—$SO_2NR^{50}R^{51}$ wherein $R^{50}$ and $R^{51}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and wherein $R^{50}$ and $R^{51}$ are optionally joined together with the nitrogen bound thereto to form a heterocyclic or substituted heterocyclic group.

"Aminosulfonylamino" refers to the group —$NR^{47}SO_2NR^{50}R^{51}$, wherein $R^{47}$ is hydrogen or alkyl; $R^{50}$ and $R^{51}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic; and, wherein $R^{50}$ and $R^{51}$ are optionally joined together with the nitrogen bound thereto to form a heterocyclic or substituted heterocyclic group.

"Amidino" refers to the group —$C(=NR^{52})NR^{50}R^{51}$, wherein $R^{50}$, $R^{51}$, and $R^{52}$ are independently selected from the group consisting of hydrogen, alkyl, substituted alkyl, alkenyl, substituted alkenyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and wherein $R^{50}$ and $R^{51}$ are optionally joined together with the nitrogen bound thereto to form a heterocyclic or substituted heterocyclic group.

"Aryl" or "Ar" refers to a monovalent aromatic carbocyclic group of from 6 to 14 carbon atoms having a single ring (e.g., phenyl) or multiple condensed rings (e.g., naphthyl or anthryl). The condensed rings may or may not be aromatic (e.g., 2-benzoxazolinone, 2H-1,4-benzoxazin-3(4H)-one-7-yl, and the like), provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkoxy, substituted alkoxy, acyl, acylamino, acyloxy, amino, substituted amino, aminocarbonyl, aminocarbonylamino, aminocarbonyloxy, aminosulfonyl, aminosulfonyloxy, aminosulfonylamino, amidino, aryl, substituted aryl, aryloxy, substituted aryloxy, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkenyl, substituted cycloalkenyl, cycloalkenyloxy, substituted cycloalkenyloxy, guanidino, halo, hydroxy, heteroaryl, substituted heteroaryl, heteroaryloxy, substituted heteroaryloxy, heterocyclic, substituted heterocyclic, heterocyclyloxy, substituted heterocyclyloxy, nitro, SO₃H, substituted sulfonyl, substituted sulfonyloxy, and thiol.

"Arylene" refers to a divalent aromatic carbocyclic group of from 6 to 14 carbon atoms having a single ring or multiple condensed rings. "Substituted arylene" refers to an arylene having from 1 to 5, preferably 1 to 3, or more preferably 1 to 2 substituents as defined for aryl groups.

"Aryloxy" refers to the group —O-aryl, wherein aryl is as defined herein. Exemplary aryloxy groups include phenoxy and naphthoxy. "Substituted aryloxy" refers to the group —O-(substituted aryl).

"Carbonyl" refers to the divalent group —C(O)— (i.e., —C(=O)—).

"Carboxyl" or "carboxy" refers to —COOH, or salts thereof.

"Carboxyl ester" or "carboxy ester" refers to the group —C(O)(O)-alkyl, —C(O)(O)-substituted alkyl, —C(O)O-alkenyl, —C(O)(O)-substituted alkenyl, —C(O)(O)-aryl, —C(O)(O)-substituted aryl, —C(O)(O)-cycloalkyl, —C(O)(O)-substituted cycloalkyl, —C(O)(O)-cycloalkenyl, —C(O)(O)-substituted cycloalkenyl, —C(O)(O)-heteroaryl, —C(O)(O)-substituted heteroaryl, —C(O)(O)-heterocyclic, and —C(O)(O)-substituted heterocyclic.

"(Carboxyl ester)amino" refers to the group —NR⁴⁷C(O)(O)-alkyl, —NR⁴⁷C(O)(O)-substituted alkyl, —NR⁴⁷C(O)O-alkenyl, —NR⁴⁷C(O)(O)-substituted alkenyl, —NR⁴⁷C(O)(O)-aryl, —NR⁴⁷C(O)(O)-substituted-aryl, —NR⁴⁷C(O)(O)-cycloalkyl, —NR⁴⁷C(O)(O)-substituted cycloalkyl, —NR⁴⁷C(O)(O)-cycloalkenyl, —NR⁴⁷C(O)(O)-substituted cycloalkenyl, —NR⁴⁷C(O)(O)-heteroaryl, —NR⁴⁷C(O)(O)-substituted heteroaryl, —NR⁴⁷C(O)(O)-heterocyclic, and —NR⁴⁷C(O)(O)-substituted heterocyclic.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic.

"Cyano" refers to the group —CN.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. "Cycloalkenyl" refers to cycloalkyl groups which are partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl and cycloalkenyl groups can be substituted or unsubstituted.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkoxy, substituted alkoxy, acyl, acylamino, acyloxy, amino, substituted amino, aminocarbonyl, aminocarbonylamino, aminocarbonyloxy, aminosulfonyl, aminosulfonyloxy, aminosulfonylamino, amidino, aryl, substituted aryl, aryloxy, substituted aryloxy, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkenyl, substituted cycloalkenyl, cycloalkenyloxy, substituted cycloalkenyloxy, guanidino, halo, hydroxy, heteroaryl, substituted heteroaryl, heteroaryloxy, substituted heteroaryloxy, heterocyclic, substituted heterocyclic, heterocyclyloxy, substituted heterocyclyloxy, nitro, SO₃H, substituted sulfonyl, substituted sulfonyloxy, and thiol.

"Cycloalkyloxy" refers to —O-cycloalkyl. "Substituted cycloalkyloxy" refers to —O-(substituted cycloalkyl).

"Cycloalkenyloxy" refers to —O-cycloalkenyl. "Substituted cycloalkenyloxy" refers to —O-(substituted cycloalkenyl).

"Guanidino" refers to the group —NHC(=NH)NH₂.

"Halo" or "halogen" refers to fluoro, chloro, bromo and iodo.

"Hydroxy" or "hydroxyl" refers to the group —OH.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)₂—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, which may or may not contain a heteroatom, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, benzofuran, indolizine or benzothiene. The heteroaryl groups can be fused to non-aromatic ring systems, which may or may not contain a heteroatom, provided that the point of attachment is through an atom of the aromatic heteroaryl group. For example, the nitrogen and/or the sulfur ring atom(s) of the heteroaryl group are optionally oxidized to provide for the N-oxide (N→O), sulfinyl, or sulfonyl moieties. Certain non-limiting examples include pyridinyl, pyrrolyl, indolyl, thiophenyl, oxazolyl, thizolyl, and furanyl.

Other heteroaryl groups include heteroaryl rings linked by a bond, such as bipyridine. Heteroaryl groups can be substituted or unsubstituted.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl. "Substituted heteroaryloxy" refers to the group —O-(substituted heteroaryl).

"Heterocycle" or "heterocyclic" or "heterocycloalkyl" or "heterocyclyl" refers to a saturated, or partially saturated, ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties. Heterocycloalkyl groups can be unsubstituted or substituted. For example, heterocycloalkyl groups can be substituted with $C_{1-6}$ alkyl, oxo (=O), nitro (—NO$_2$), or sulfonyl (—S(O)$_2$—), among many others.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocyclyl. "Substituted heterocyclyloxy" refers to the group —O-(substituted heterocyclyl).

Examples of heterocyclyls and heteroaryls include, but are not limited to, azetidine, pyrrole, furan, thiophene, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Spirocycloalkyl" and "spiro ring systems" refers to divalent cyclic groups from 3 to 10 carbon atoms having a cycloalkyl or heterocycloalkyl ring with a spiro union (the union formed by a single atom which is the only common member of the rings) as exemplified by the following structure:

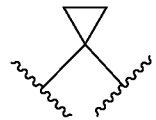

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic. Substituted sulfonyl includes groups such as methyl-SO$_2$—, phenyl-SO$_2$—, and 4-methylphenyl-SO$_2$—.

"Substituted sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, and —OSO$_2$-substituted heterocyclic.

As used herein, the term "saccharide" refers to a sugar, such as a monosaccharide, a disaccharide, an oligosaccharide or a polysaccharide. Monosaccharides include, but are not limited to, glucose, ribose and fructose. Disaccharides include, but are not limited to, sucrose and lactose. Oligosaccharides refers to 2 to 10 sugars linked together preferably through an alpha linkage. Examples of oligosaccharides include maltose, lactose, sucrose, and the like. Polysaccharides include, but are not limited to, cellulose, hemicellulose and lignocellulose or starch. Saccharides or sugars useful in the present invention include any and all naturally occurring sugars, such as, but not limited to, glucose, glucuronic acid, iduronic acid, galactose, fucose, glucosamine, N-acetylglucosamine, fructose, sialic acid, including aldol and pyranose forms thereof, as well as D and L isomers thereof.

A substituted ring can be substituted with one or more fused and/or spiro cycles. Such fused cycles include a fused cycloalkyl, a fused heterocyclyl, a fused aryl, a fused heteroaryl ring, each of which rings can be unsubstituted or substituted. Such spiro cycles include a fused cycloalkyl and a fused heterocyclyl, each of which rings can be unsubstituted or substituted.

The groups defined above can optionally be substituted by any suitable number and type of substituents. Representative substituents include, but are not limited to, alkyl, alkenyl, alkynyl, aryl, cycloalkyl, heteroalkyl, heteroaryl, heterocycloalkyl, halogen, haloalkyl, haloalkoxy, —OR', =O, —OC(O)R', —(O)R', —O$_2$R', —ONR'R", —OC(O)NR'R", =NR', =N—OR', —NR'R", —NR"C(O)R', —NR'—(O)NR"R'", —NR"C(O)OR', —NH—(NH$_2$)=NH, —NR'C(NH$_2$)=NH, —NH—(NH$_2$)=NR', —SR', —S(O)R', —S(O)$_2$R', —S(O)$_2$NR'R", —NR'S(O)$_2$R", —N$_3$ and —NO$_2$. R', R" and R'" each independently refer to hydrogen, unsubstituted alkyl, such as unsubstituted $C_{1-6}$ alkyl. Alternatively, R' and R", or R" and when attached to the same nitrogen, are combined with the nitrogen to which they are attached to form a heterocycloalkyl or heteroaryl ring, as defined above Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. In other words, each of the above definitions is constrained by a limitation that, for example, substituted aryl groups are limited to -substituted aryl-(substituted aryl)-substituted aryl.

It is understood that the above definitions are not intended to include impermissible substitution patterns (e.g., methyl substituted with 5 fluoro groups). Such impermissible substitution patterns are well known to the skilled artisan.

"Tautomer" refers to constitutional isomers of organic compounds that readily convert by the chemical reaction of tautomerization or tautomerism. The reaction commonly results in the formal migration of a hydrogen atom or proton, accompanied by a switch of a single bond and adjacent double bond. Tautomerism is a special case of structural isomerism and because of the rapid interconversion; tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic acid tautomerism in heterocyclic rings), enamine and enamine and anomers of reducing sugars.

"Stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection or their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which thy rotate polarized light and how they interact with different optical isomers of other compounds. Diastereomers and stereoisomers not related through a reflection operation, they are not mirror images of each other. These include meso compounds, cis- and trans-(E- and Z-) isomers, and non-enantiomeric optical isomers. Diastereomers seldom have the same physical properties. In terms of the present disclosure, stereoisomers may refer to enantiomers, diastereomers or both. Stereoisomers are often obtained in partially purified form. For the compounds of this invention that possess stereoisomers, such partially purified forms include those having 60%, 70%, 80%, 90% or 95% of one dominant stereoisomer.

The compounds of the present invention can be in salt form, such as acid or base salts of the compounds of the present invention. "Pharmaceutically acceptable salt" refers to salts of active compounds that are prepared with acids or bases, depending upon the particular substituents found on the compounds described herein. Illustrative examples of pharmaceutically acceptable salts acting as counter-ions to negative charge groups include sodium, potassium, calcium, ammonium, organic amino, or magnesium salt, or other well-known salts. Examples of pharmaceutically acceptable salts acting as counter-ions to positively charged groups include carboxylic acids such as acetic acid, propionic acid, isobutyric acid, maleic acid, malonic acid, benzoic acid, succinic acid, suberic acid, fumaric acid, lactic acid, citric acid, tartaric acid, oxalic acid, and the like. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The compounds of the present invention can exist in unsolvated forms, or anhydrous forms, as well as solvated forms, including hydrated forms. Hydrates, as the name infers, refer to complexation of molecules of water with each molecule of this invention. Solvates refer to complexation with an organic solvent such as methanol, ethanol, and isopropanol, and the like. In general, the solvated forms are equivalent to unsolvated forms and are intended to be encompassed within the scope of the present invention. Certain compounds of the present invention may exist in multiple crystalline or amorphous forms. In general, all physical forms (e.g., anhydrates, solvates and hydrates) are equivalent for the uses contemplated by the present invention and are intended to be within the scope of the present invention.

"Positional isomers" or "constitutional isomers" refers to different compounds which have the same numbers of, and types of, of atoms, and hence the same molecular weight, but the atoms are connected differently.

As used herein, the term "beta-amyloid" refers to peptides of 36 to 43 amino acids that are involved in the formation of fibrils, plaques, and/or amyloid deposits by being enzymatically cleaved from amyloid precursor protein. The term also encompasses peptides having substantial similarity to amyloid-like proteins, such as, for example, structural variants. In some cases, the peptides occur naturally or can be synthetically constructed. The term beta-amyloid also includes amyloidogenic proteins and proteins that produce amyloid-like morphology.

As used herein, "substantial similarity" means that two peptide sequences, when optimally aligned, share at least 50% sequence identity, or at least 60% sequence identity, or at least 70% sequence identity, or at least 80% sequence identity, or at least 90% sequence identity, or at least 95% sequence identity or more (e.g., 99% sequence identity). Preferably, residue positions, which are not identical, differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains include methionine and cysteine. Preferred conservative amino acids substitution groups are valine-leucine-isoleucine; phenylalanine-tyrosine; lysine-arginine; alanine-valine; and asparagine-glutamine. In some cases, residue positions, which are not identical are also composed of peptide analogs, including unnatural amino acids or derivatives thereof. Analogs typically differ from naturally occurring peptides at one, two, or a few positions, often by virtue of conservative substitutions. Some analogs also include unnatural amino acids or modifications of N or C terminal amino acids one, two, or a few positions. Examples of unnatural amino acids are D-amino acids, alpha, alpha-disubstituted amino acids, N-alkyl amino acids, lactic acid, 4-hydroxyproline, y-carboxyglutamate, epsilon-N,N,N-trimethyllysine, epsilon-N-acetyllysine, O-phosphoserine, N-formylmethionine, 3-methylhistidine, 5-hydroxylysine, omega-N-methylarginine, and isoaspartic acid.

As used herein, the term "stereochemically pure" as used herein with reference to a compound, means the compound or a composition thereof comprises predominantly one stereoisomer of the compound and is substantially free of other stereoisomer(s) of that compound. For example, a stereochemically pure composition of a compound having one chiral center will be substantially free of the opposite enantiomer of the compound. A stereochemically pure composition of a compound having two or more chiral centers will be substantially free of other diastereomers of the compound. A typical stereochemically pure compound comprises about 80% by weight or greater of one stereoisomer of the compound and about 20% by weight or less of other stereoisomer(s) of the compound. For example, in various embodiments, a stereochemically pure compound comprises 90% by weight or greater of one stereoisomer of the compound and about 10% by weight or less of the other stereoisomer(s) of the compound; about 95% by weight or greater of one stereoisomer of the compound and about 5% by weight or less of the other stereoisomer(s) of the compound; about 97% by weight or greater of one stereoisomer of the compound and about 3% by weight or less of the other stereoisomer(s) of the compound; about 98% by weight or greater of one stereoisomer of the compound and about 2% by weight or less of the other stereoisomer(s) of the compound, and about 99% by weight or greater of one stereoisomer of the compound and about 1% by weight or less of the other stereoisomer(s) of the compound.

The terms "administering" or "administration" refers to any form of administration including oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the patient or subject. Suitable routes of administration are well known to the skilled artisan.

"Therapeutically effective amount," "therapeutically effective dose," "therapeutically sufficient amount," "therapeutically sufficient dose," or "effective or sufficient amount or dose" refer to an amount or dose of a compound of the present invention, or compositions thereof, that produces therapeutic effects for which it is administered. For example, the therapeutically effective amount or dose can be an amount sufficient to increase dendritic spine formation, and/or an amount that reduces the neurotoxicity of abnormal protein structures, protein aggregates, or protein misfolding, such as amyloid plaques and/or amyloid deposits. Such deposits correlate to the patient's risk of, or presence of, diseases or conditions associated with beta-amyloid proteins, such as neurological diseases or conditions. In some cases, such diseases or conditions are referred to as amyloid based diseases or conditions. These diseases and conditions include, for example, neurological diseases such as Alzheimer's disease, Parkinson's disease, Huntington's disease, diseases and/or conditions characterized by a loss of cognitive memory capacity such as, for example, mild cognitive impairment, Lewy body dementia, Down's syndrome, hereditary cerebral hemorrhage with amyloidosis (Dutch type) and the Guam Parkinson-Dementia complex. Other diseases and/or conditions which are based on or associated with beta-amyloid are progressive supranuclear palsy, multiple sclerosis, Creutzfeld Jacob disease, HIV-related dementia, ALS (amyotrophic lateral sclerosis), inclusion-body myositis (IBM), Adult Onset Diabetes, senile cardiac amyloidosis, endocrine tumors, and other diseases, including amyloid-associated ocular diseases that target different tissues of the eye, such as the visual cortex, including cortical visual deficits; the anterior chamber and the optic nerve, including glaucoma; the lens, including cataract due to amyloid-like deposition; the vitreous, including ocular amyloidosis; the retina, including primary retinal degenerations and macular degeneration, in particular age-related macular degeneration; the optic nerve, including optic nerve drusen, optic neuropathy and optic neuritis; and the cornea, including lattice dystrophy as well as cognitive loss due to brain injury either alone or in the aggregate (e.g., cumulative brain injuries due to repeated concussions).

The exact dosage and frequency of administration of the compounds of the present invention, or compositions thereof, will depend on the severity of the condition treated, the age, weight, and sex of the patient, as well as other factors well known in the art, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

The compounds and/or compositions of the present invention can be used alone or in combination with one or more further therapeutic agents. When used in combination, the compounds and/or compositions of the present invention can be administered simultaneously (i.e. concurrently) with one or more further therapeutic agents or consecutively with one or more further therapeutic agents. Consecutive administration is intended to encompass various orders of administration of the therapeutic agent(s) and the compound(s)/compositions of the invention to the subject.

The term "spinogenesis" refers to the growth of new dendritic spines on neurons.

As used herein, the term "dendrite" refers to the branched extension of a neuron cell. Dendrites are typically responsible for receiving electrochemical signals transmitted from the axon of an adjacent neuron. The terms "dendritic spines" or "dendrite spines" refer to protoplasmic protuberances on a neuron cell (e.g., on a dendrite). In some embodiments, dendritic spines may be described as having a membranous neck which may be terminated with a capitulum (e.g., head), which are classified according to their shape: headless, thin, stubby, mushroom, or branched. Dendritic spinal density therefore refers to the total number of dendritic spines per unit length of a neuron cell.

The term "dendritic spine formation" and the like refers to processes which lead to an increased number of dendritic spines or increased development of dendritic spines. The term "dendritic spine morphology" and the like refers to the physical characterization of a dendritic spine (e.g., shape and structure).

"Patient" or "subject in need thereof" refers to a living organism suffering from or prone to a condition that can be treated by administration of a compound or a pharmaceutical composition thereof, as provided herein. Non-limiting examples include humans, other mammals and other non-mammalian animals.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Disorder" or "condition" refer to a state of being or health status of a patient or subject capable of being treated with the compounds of the present invention. Examples of disorders or conditions include, but are not limited to low dendritic spine density of neurons, neurotoxicity of beta-amyloid peptides to neurons, and traumatic brain injury.

"Traumatic brain injury" or "TBI" refer to an acquired brain injury or a head injury, when a trauma causes damage to the brain. Trauma includes, e.g., post-head trauma, impact trauma, and other traumas to the head such as, for example, traumas caused by accidents and/or sports injuries, concussive injuries, penetrating head wounds, brain tumors, stroke, heart attack, meningitis, viral encephalitis, and other conditions that deprive the brain of oxygen. In a particular embodiment, the trauma is an external, physical force. In another embodiment, the trauma is a "blast-induced traumatic brain injury," which refers to a TBI caused by the direct or indirect exposure to an explosion.

"Blunt force impact" refers to a brain injury when the head suddenly and violently hits an object but the object does not break through the skull.

"Concussion" refers to a mild form of traumatic brain injury resulting in temporary impairment of neurological function which quickly resolves by itself, and where there are generally no gross structural changes to the brain as the result of the condition. A concussion is generally considered to occur when there is a blow to the head or other forceful event, resulting in loss of consciousness for less than 30 minutes.

"Assessment" and "test" refer to an evaluation used to determine the severity of a traumatic brain injury, the details of which are described herein.

"An amount sufficient to reduce the symptoms of traumatic brain injury" refers to the quantity of a compound administered to a patient suffering from a traumatic brain injury necessary to observe a reduction of the symptoms of traumatic brain injury in a patient. "Symptoms" of a traumatic brain injury may include elevated levels of biomarkers in a patient's blood. Examples of biomarkers that become elevated in the blood of a patient suffering from a traumatic brain injury are GFAP and UCH-L1. Other symptoms of a traumatic brain injury are the deficits of the following functional domains: physical, visual, auditory, neurobehavioral, cognitive-communication, and sleep. The details of biomarkers and each functional domain are described herein. A sufficient amount of a compound administered to a patient having traumatic brain injury symptoms will cause at least a 20% to 30% reduction in the symptoms compared to a statistically significant cohort of patients with a traumatic brain injury who are not administered a sufficient amount of compounds.

The embodiments, illustratively described herein, may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

Where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of this invention. This includes the generic description of this invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

II. COMPOUNDS

In some embodiments, the present invention provides a compound of Formula I and/or Formula IA:

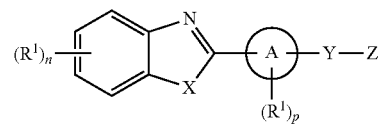

I

IA

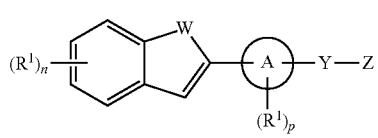

or a pharmaceutically acceptable salt, solvate, and/or an N-oxide thereof, wherein subscripts n and p are independently selected from 0, 1 or 2;

each $R^1$ is independently selected from the group consisting of halo, alkyl, substituted alkyl, alkoxy, substituted alkoxy, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, thiol, and nitro;

A is an arylene or heteroarylene, having 1 to 4 heteroatoms;

W is selected from the group consisting of —O—, —S—, —SO—, —S(O)$_2$—, and —NR$^{12}$—, wherein R$^{12}$ is selected from the group consisting of hydrogen, alkyl, substituted alkyl, aryl, substituted aryl, heteroaryl, substituted heteroaryl, heterocycloalkyl, and substituted heterocycloalkyl;

X is selected from the group consisting of —O—, —S—, —SO—, —S(O)$_2$—, and —NR$^{12}$—, wherein R$^{12}$ is as defined above, provided that when A is arylene, and Y is —S— or —NR$^{12}$—, then X is not —S—;

Y is selected from the group consisting of —O—, —S—, —SO—, S(O)$_2$—, and —NR$^{12}$—, wherein R$^{12}$ is as defined above; and Z is selected from the group consisting —N(CH$_3$)$_2$ CH$_2$CH$_2$OC(O)CH$_3$ and —(CH$_2$CH(R$^{13}$)O)$_q$-T, wherein subscript q is an integer selected from 1 to 100, R$^{13}$ is selected from the group consisting of hydrogen and methyl, and T is selected from the group consisting of hydrogen, alkyl, substituted alkyl, -L-monosaccharide, and -L-oligosaccharide, wherein L is selected from the group consisting of a bond, phosphate, and sulfate.

In some embodiments, the present invention provides a compound according to Formula II, Formula III, Formula IV, Formula V, and/or Formula VI:

II

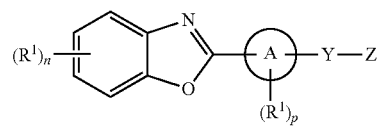

III

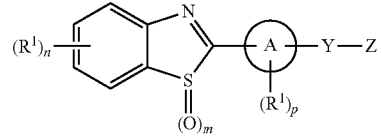

IV

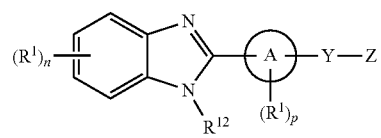

V

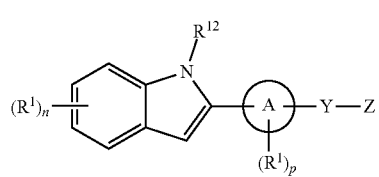

VI

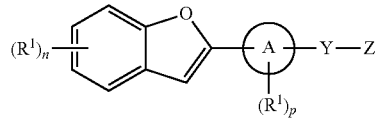

or a pharmaceutically acceptable salt, solvate, and/or an N-oxide thereof, wherein
$R^1$, $R^{12}$, A, Y, Z, n and p are as defined above; and
subscript m is selected from 0, 1 or 2.

In some embodiments, A is a heteroaryl (heteroarylene) group selected from pyridinylene, 1,3-imidazolylene, furanylene, pyrrolyene, thiophenylene, indolylene, and the like. In some embodiments, A is an aryl (arylene) group, such as phenylene or naphthalyene.

In some embodiments, the invention provides a compound of Formula I and/or Formula IA, or a pharmaceutically acceptable salt and/or solvate thereof, wherein the compound is selected from:

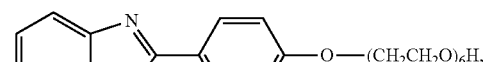

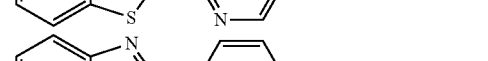

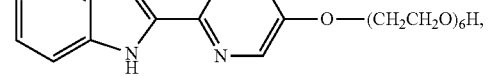

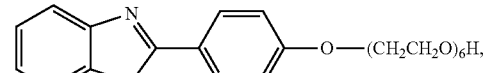

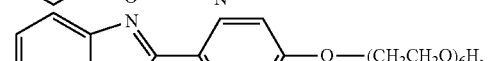

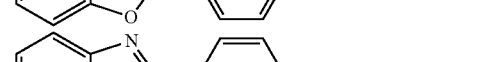

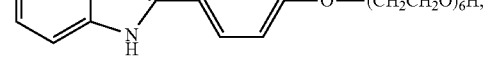

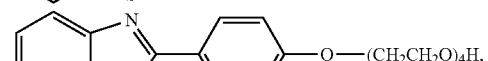

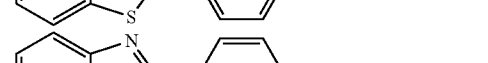

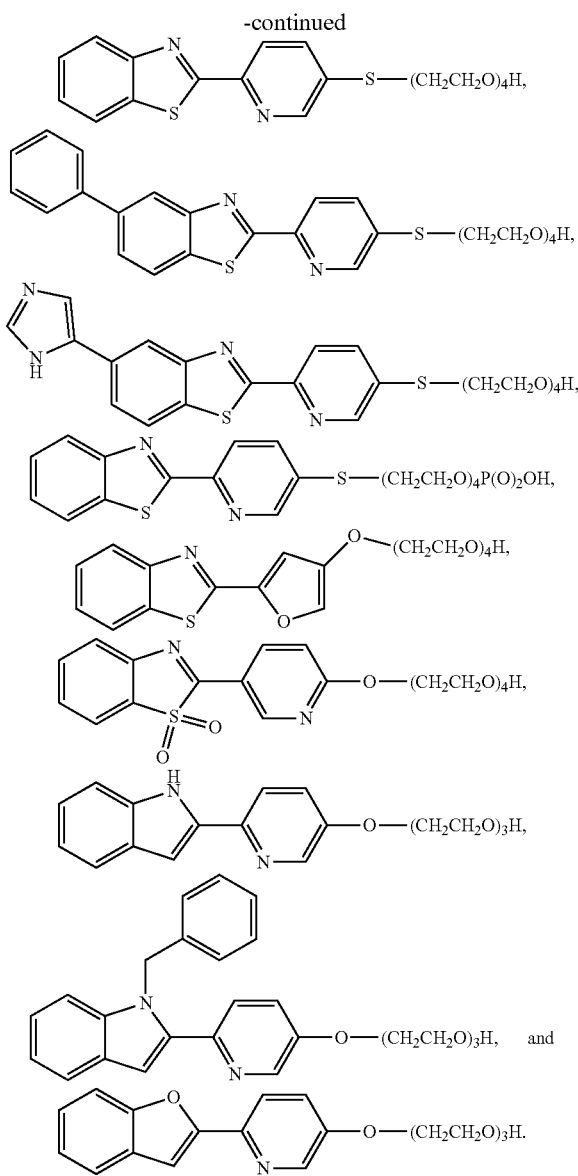

In some embodiments, the present invention provides a compound of Formula VII:

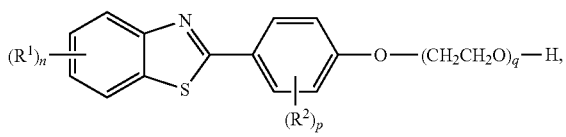

(VII)

or a pharmaceutically acceptable salt or solvate thereof, wherein: subscripts n and p are independently selected from 0 to 4; subscript q is an integer selected from 1 to 20; and each $R^1$ and $R^2$ are independently selected from the group consisting of halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro.

In some embodiments of the invention, each $R^1$ and $R^2$ of Formula (VII) are independently selected from the group consisting of —F; —Cl; —Br; —I; substituted or unsubstituted alkyl (e.g. $C_1$-$C_8$, $C_1$-$C_6$, $C_1$-$C_4$, or $C_1$-$C_2$); substituted or unsubstituted alkenyl (e.g., vinyl (ethenyl), propenyl, isopropenyl, 1-butenyl, 2-butenyl, isobutenyl, butadienyl, 1-pentenyl, 2-pentenyl, isopentenyl, 1,3-pentadienyl, or 1,4-pentadienyl); substituted or unsubstituted alkoxy (e.g., methoxy, ethoxy, n-propoxy, isopropoxy, n-butoxy, t-butoxy, sec-butoxy, or n-pentoxy); acyl; acylamino; aminocarbonyl (e.g., amide or substituted amide); aminosulfonyl (e.g., sulfonamide or substituted sulfonamide); amino, substituted amino; substituted or unsubstituted aryl (e.g., phenyl, naphthyl, anthryl, 2-benzoxazolinone, or 2H-1,4-benzoxazin-3 (4H)-one-7-yl); carboxyl; carboxyl ester; cyano; substituted or unsubstituted cycloalkyl (e.g., cyclopropyl, cyclobutyl, cyclopentyl, cyclohexyl, cyclooctyl, norbornane, [2.2.2] bicyclooctane, decahydronaphthalene, adamantine, cyclobutene, cyclopentene, cyclohexene, cyclohexadiene, cycloheptene, cycloheptadiene, cyclooctene, cyclooctadiene (1,3-, 1,4- and 1,5-isomers), norbornene, or norbornadiene); substituted or unsubstituted heteroaryl (e.g., pyrrole, pyridine, imidazole, pyrazole, triazole, tetrazole, pyrazine, pyrimidine, pyridazine, triazine, thiophene, furan, thiazole, isothiazole, oxazole, or isoxazole); substituted or unsubstituted heterocyclyl (e.g., aziridine, azetidine, pyrrolidine, piperidine, azepane, azocane, quinuclidine, pyrazolidine, imidazolidine, piperazine, oxirane, oxetane, tetrahydrofuran, oxane, oxepane, thiirane, thietane, thiolane, thiane, oxazolidine, isoxazolidine, thiazolidine, isothiazolidine, dioxolane, dithiolane, morpholine, thiomorpholine, dioxane, or dithiane); hydroxyl; sulfonyl, substituted sulfonyl; thiol; thioalkyl; and nitro.

In some embodiments of the invention, each $R^1$ and $R^2$ of Formula (VII) are independently selected from the group consisting of —F; —Cl; —Br; —I; substituted or unsubstituted alkyl (e.g. methyl, ethyl, n-propyl, isopropyl, n-butyl, t-butyl, isobutyl, sec-butyl); substituted or unsubstituted alkenyl (e.g., vinyl (ethenyl), propenyl, isopropenyl, 1-butenyl, 2-butenyl, isobutenyl, or butadienyl); substituted or unsubstituted alkoxy (e.g., methoxy, ethoxy, n-propoxy, isopropoxy, n-butoxy, t-butoxy, sec-butoxy, or n-pentoxy); acyl; acylamino; aminocarbonyl (e.g., amide or substituted amide); aminosulfonyl (e.g., sulfonamide or substituted sulfonamide); amino, substituted amino; substituted or unsubstituted aryl (e.g., phenyl, naphthyl, anthryl, or 2-benzoxazolinone); carboxyl; carboxyl ester; cyano; substituted or unsubstituted cycloalkyl (e.g., cyclopropyl, cyclobutyl, cyclopentyl, or cyclohexyl); hydroxyl; sulfonyl, substituted sulfonyl; thiol; thioalkyl; and nitro.

In some embodiments of the invention, each $R^1$ and $R^2$ of Formula (VII) are independently selected from the group consisting of —F; —Cl; —Br; —I; methyl; ethyl; n-propyl; isopropyl; substituted lower alkyl; vinyl; propenyl; methoxy; ethoxy; n-propoxy; acyl; acylamino; aminocarbonyl; aminosulfonyl; amino; substituted amino; phenyl; carboxyl; carboxyl ester; cyano; cyclopropyl; cyclobutyl; cyclopentyl; cyclohexyl; hydroxyl; sulfonyl; substituted sulfonyl; thiol; thioalkyl; and nitro.

In some embodiments of the invention, each $R^1$ and $R^2$ of Formula (VII) are independently selected from the group consisting of halo, —$CH_3$—OH, —$CH_2SO_2NH_2$, —$SO_2NH_2$, —$CH_2CH_3$, cyclopentyl, —$CF_3$, —CN, —$CHCH_2$, —$CH_2CHCH_2$, phenyl, —$CO_2H$, —$CH_2CO_2H$, —$CH_2CONH_2$, —$COOCH_3$, —$COCH_3$, —$(CH_2)_{20}CH_3$, —CONH$_2$, —CON(CH$_3$)$_2$, —CH$_2$SO$_2$N(CH$_3$)$_2$, —OCH$_3$, —OCF$_3$, —OCH(CH$_3$)$_2$, —N(CH$_3$)$_2$, —NHCOCH$_3$, —NO$_2$, —SCH$_3$, —SO$_2$CH$_3$, and —SO$_2$N(CH$_3$)$_2$.

In some embodiments of the invention, each R$^1$ of Formula (VII) is independently selected from the group consisting of halo, —OH, —CN, phenyl, —CHCH$_2$, —COCH$_3$, —COOCH$_3$, —CH$_2$SO$_2$NH$_2$, —NHCOCH$_3$, —N(CH$_3$)$_2$, —SCH$_3$, and —SO$_2$NH$_2$; and each R$^2$ of Formula (VII) is independently selected from the group consisting of halo, —CH$_3$, —CH$_2$CH$_3$, cyclopentyl, —CF$_3$, —CN, —CHCH$_2$, —CH$_2$CHCH$_2$, phenyl, —CO$_2$H, —CH$_2$CO$_2$H, —CH$_2$CONH$_2$, —COOCH$_3$, —COCH$_3$, —(CH$_2$)$_{20}$CH$_3$, —CONH$_2$, —CON(CH$_3$)$_2$, —CH$_2$SO$_2$N(CH$_3$)$_2$, —OCH$_3$, —OCF$_3$, —OCH(CH$_3$)$_2$, —N(CH$_3$)$_2$, —NHCOCH$_3$, —NO$_2$, —SCH$_3$, —SO$_2$CH$_3$, and —SO$_2$N(CH$_3$)$_2$.

In some embodiments, subscripts n and p of Formula (VII) are independently selected from 0 to 4. In some embodiments, subscripts n and p are independently 0, 1, 2, 3, or 4. In some embodiments, subscripts n and p are independently 0, 1, 2, or 3. In some other embodiments, subscripts n and p are independently 0, 1, or 2. In some embodiments, subscripts n and p are independently 0 or 1. In some embodiments, subscripts n and p are independently 0 or 1, provided that subscripts n and p are not both 1. In some embodiments, subscript n is 1 and subscript p is 0. In other embodiments, subscript n is 0 and subscript p is 1. In some embodiments, subscripts n and p are both 0.

In some embodiments, subscript q of Formula (VII) is an integer from 1 to 20. In some embodiments, subscript q is an integer from 1 to 15, 2 to 14, 3 to 13, 4 to 12, 5 to 11, 6 to 10, or 7 to 9. In some embodiments, subscript q can be an integer from 2 to 12, 2 to 10, 2 to 8, 2 to 6, 2 to 5, or 2 to 4. In other embodiments, subscript q can be 1, 2, 3, 4, 5, 6, 7, 8, 9, 10, 11, 12, 13, 14, 15, 16, 17, 18, 19, or 20. In some embodiments, subscript q can be an integer from 2 to 8. In other embodiments, subscript q can be an integer from 3 to 6. In other embodiments, subscript q can be an integer from 4 to 6. In other embodiments, subscript q can be 4 or 6.

In some embodiments, the present invention provides a compound of Formula VII:

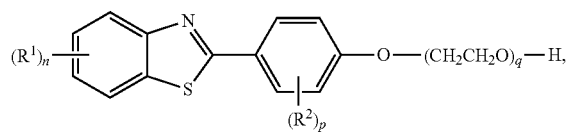

(VII)

or a pharmaceutically acceptable salt or solvate thereof, wherein: subscripts n and p are independently selected from 0, 1 or 2; subscript q is an integer selected from 2 to 8; and each R$^1$ and R$^2$ are independently selected from the group consisting of halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro.

In some embodiments of the invention, subscript q of Formula (VII) can be an integer selected from 3 to 6; subscripts n and p are independently selected from 0, 1 or 2; R$^1$ is selected from the group consisting of halo, —OH, —CN, phenyl, —CHCH$_2$, —COCH$_3$, —COOCH$_3$, —CH$_2$SO$_2$NH$_2$, —NHCOCH$_3$, —N(CH$_3$)$_2$, —SCH$_3$, and —SO$_2$NH$_2$; and R$^2$ is selected from the group consisting of halo, —CH$_3$, —CH$_2$CH$_3$, cyclopentyl, —CF$_3$, —CN, —CHCH$_2$, —CH$_2$CHCH$_2$, phenyl, —CO$_2$H, —CH$_2$CO$_2$H, —CH$_2$CONH$_2$, —COOCH$_3$, —COCH$_3$, —(CH$_2$)$_{20}$CH$_3$, —CONH$_2$, —CON(CH$_3$)$_2$, —CH$_2$SO$_2$N(CH$_3$)$_2$, —OCH$_3$, —OCF$_3$, —OCH(CH$_3$)$_2$, —N(CH$_3$)$_2$, —NHCOCH$_3$, —NO$_2$, —SCH$_3$, —SO$_2$CH$_3$, and —SO$_2$N(CH$_3$)$_2$.

In some embodiments of the invention, subscript q of Formula (VII) can be an integer selected from 3 to 6; subscripts n and p are independently selected from 0 or 1, provided that subscripts n and p are not both 1; R$^1$ is selected from the group consisting of halo, —OH, —CN, phenyl, —CHCH$_2$, —COCH$_3$, —COOCH$_3$, —CH$_2$SO$_2$NH$_2$, —NHCOCH$_3$, —N(CH$_3$)$_2$, —SCH$_3$, and —SO$_2$NH$_2$; and R$^2$ is selected from the group consisting of halo, —CH$_3$, —CH$_2$CH$_3$, cyclopentyl, —CF$_3$, —CN, —CHCH$_2$, —CH$_2$CHCH$_2$, phenyl, —CO$_2$H, —CH$_2$CO$_2$H, —CH$_2$CONH$_2$, —COOCH$_3$, —COCH$_3$, —(CH$_2$)$_{20}$CH$_3$, —CONH$_2$, —CON(CH$_3$)$_2$, —CH$_2$SO$_2$N(CH$_3$)$_2$, —OCH$_3$, —OCF$_3$, —OCH(CH$_3$)$_2$, —N(CH$_3$)$_2$, —NHCOCH$_3$, —NO$_2$, —SCH$_3$, —SO$_2$CH$_3$, and —SO$_2$N(CH$_3$)$_2$.

In some embodiments, the compound of Formula (VII), or a pharmaceutically acceptable salt or solvate thereof, can be selected from:

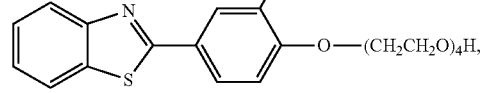

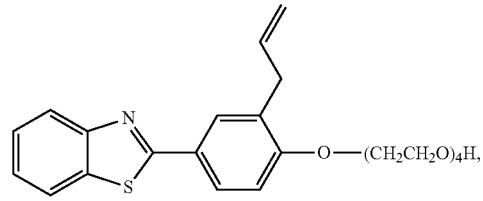

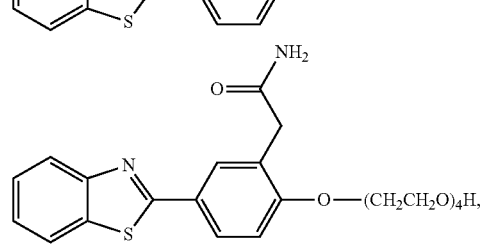

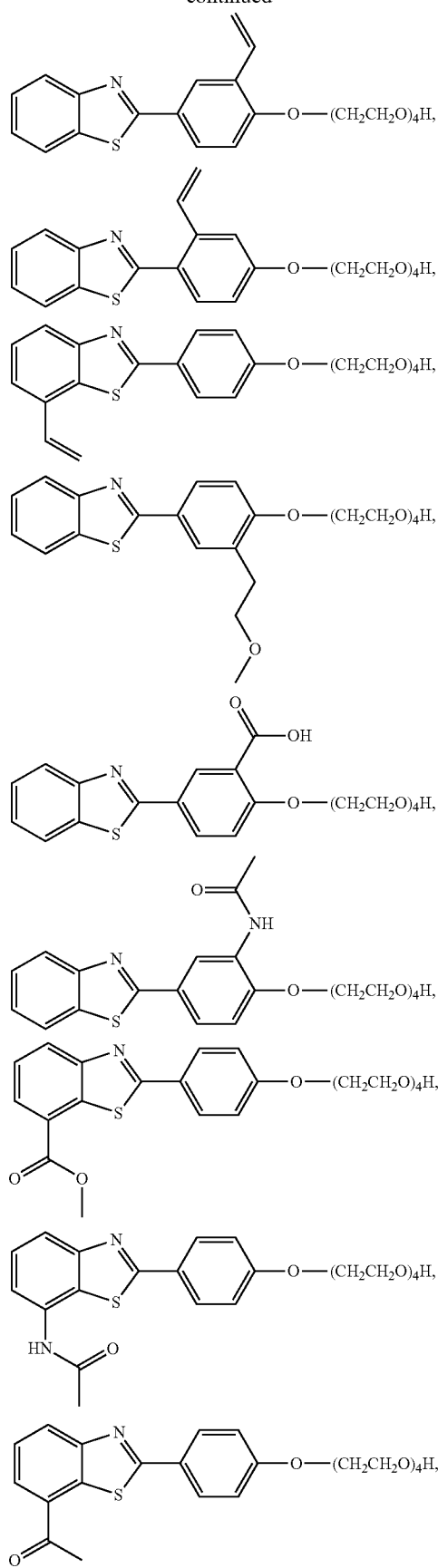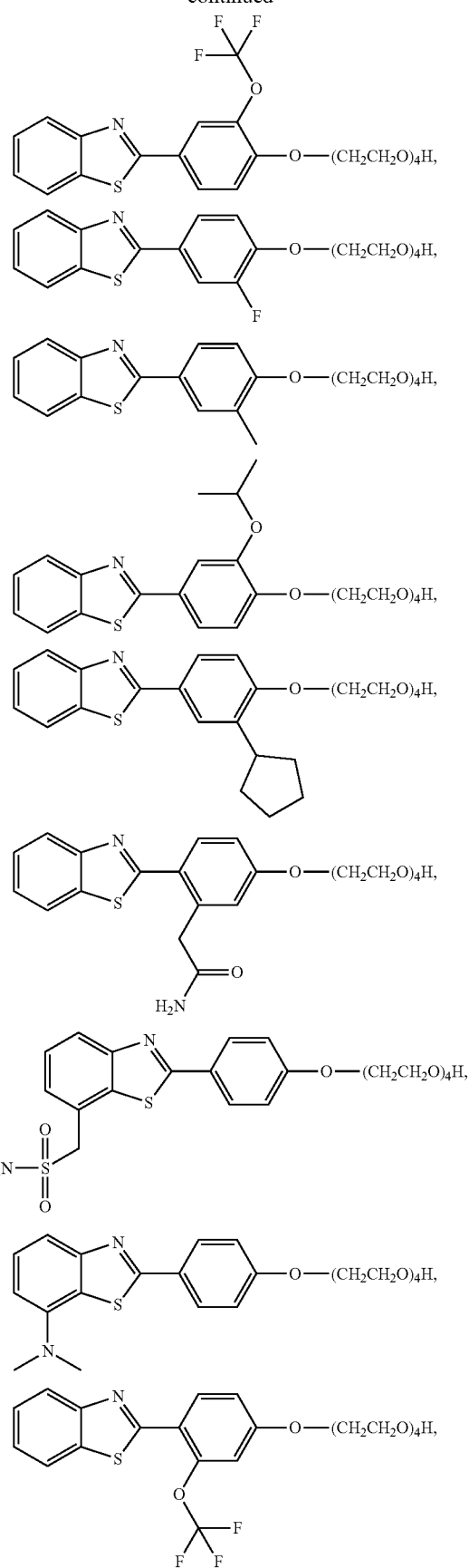

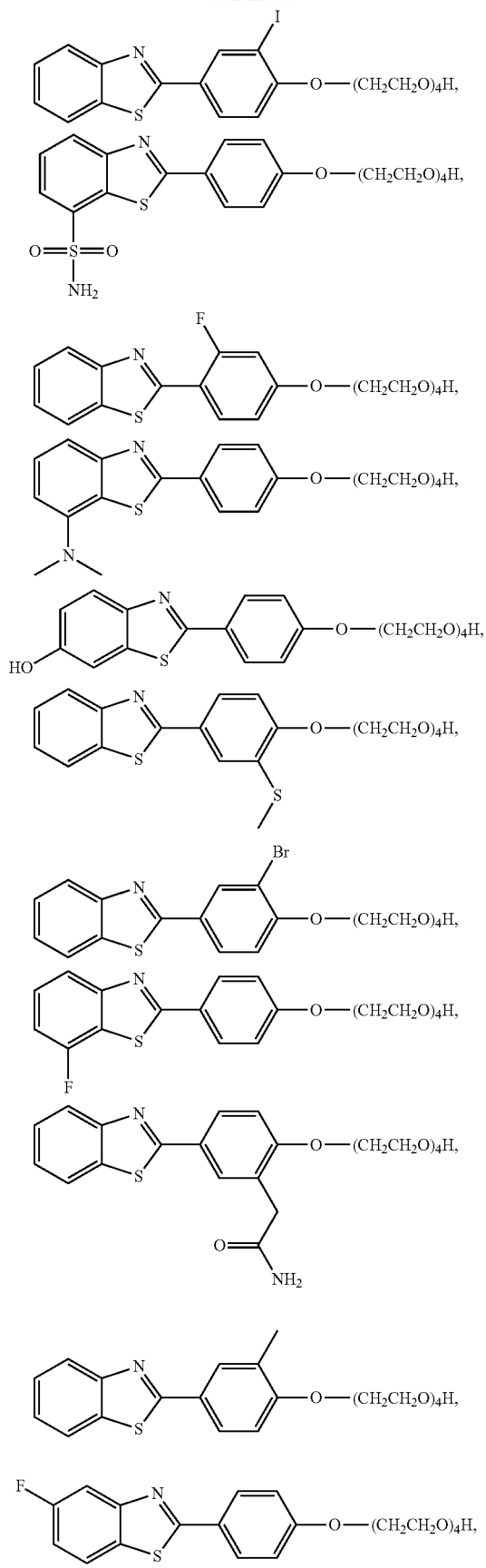

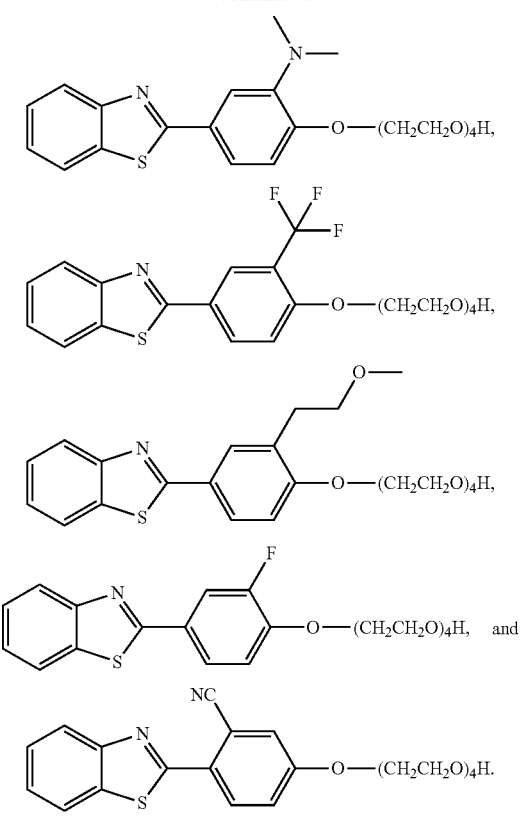

In some embodiments of the invention, each $R^1$ of Formula (VII) is independently selected from the group consisting of halo, —$CH_3$, —$OCH_3$, phenyl, and —CN; and each $R^2$ of Formula (VII) is independently selected from the group consisting of halo, —$CH_3$, —$CF_3$, —$OCH_3$, —$OCF_3$, —$CHCH_2$, —$CH_2CHCH_2$, phenyl, and —$NO_2$.

In some embodiments, the present invention provides a compound, or a pharmaceutically acceptable salt or solvate thereof, according to Formula VIIa:

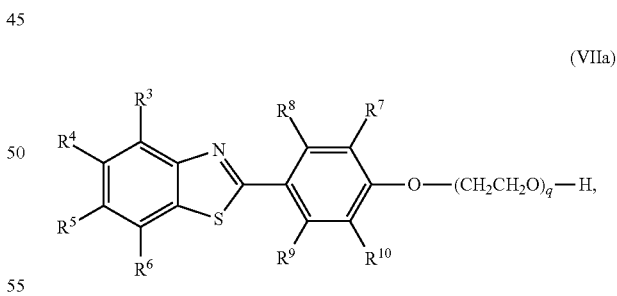

wherein: subscript q is an integer selected from 4 or 6; $R^3$, $R^4$, $R^5$, and $R^6$ are independently selected from the group consisting of hydrogen, halo, —$CH_3$, and —$OCH_3$; and, $R^7$, $R^8$, $R^9$ and $R^{10}$ are independently selected from the group consisting of hydrogen, halo, —$CH_3$, —$CF_3$, —$OCH_3$, —$OCF_3$, phenyl, —$NO_2$; wherein at least six of said R groups are hydrogen.

In some embodiments, the compound of Formula (VII) or (VIIa), or pharmaceutically acceptable salt or solvate thereof, has the formula:

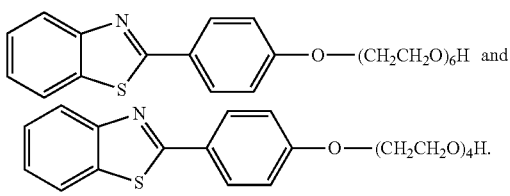

In some embodiments, the compound of Formula (VII) or (VIIa), or pharmaceutically acceptable salt or solvate thereof, has the formula:

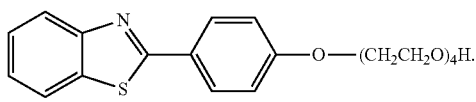

III. SYNTHESIS

The compounds of the present invention can be prepared from readily available starting materials by a variety of methods known to one of skill in the art (see *Comprehensive Organic Transformations* by Richard C. Larock, 1989) or by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. One of skill in the art will appreciate that other methods of making the compounds and alternative reaction conditions (e.g., reaction temperatures, times, molar ratios of reactants, solvents, pressures, and the like) are useful in the present invention.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T.W. Greene and P.G.M. Wuts, Protecting Groups in Organic Synthesis, Third Edition, Wiley, New York, 1999, and references cited therein.

If the compounds of this invention contain one or more chiral centers, such compounds can be prepared or isolated as pure stereoisomers (i.e., as individual enantiomers or as stereoisomer-enriched mixtures). All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials and reagents used in preparing the compounds of the invention are available from commercial suppliers, such as, for example, Sigma-Aldrich (St. Louis, Missouri, USA), Bachem (Torrance, California, USA), and Emka-Cheme, (St. Louis, Missouri, USA). Alternatively, the starting materials and reagents used in preparing the compounds of the invention are prepared by methods known to those skilled in the art following procedures set forth in references such as Fieser and Fieser's *Reagents for Organic Synthesis*, Vol. 1-28 (Wiley, 2016); March's *Advanced Organic Chemistry*, $7^{th}$ Ed. (Wiley, 2013); Rodd's *Chemistry of Carbon Compounds*, Volumes 1-5, and *Supplementals* (Elsevier Science Publishers, 1989); and Larock's *Comprehensive Organic Transformations*, $2^{nd}$ Ed. (Wiley, 1999). The starting materials and the intermediates of the reaction can be isolated and purified if desired using conventional techniques including, but not limited to, filtration, distillation, crystallization, chromatography and the like. Such materials can be characterized using conventional means, including measuring physical constants and obtaining spectral data.

Compounds of the instant invention may be prepared by the following approaches, summarized in Scheme 1 and described below. As shown in Scheme 1, the hydroxyl group of compound (i) can be deprotonated by any suitable reagent to form the corresponding oxide (ii), wherein $R^1$, A, X, n and p are as defined herein, and E is a counter cation (e.g., sodium, lithium, and potassium). For example, contacting compound (i) with metallic sodium, sodium hydride, or a strong base such as lithium diisopropylamide (LDA), under suitable conditions results in the corresponding oxide (ii). Alternatively, the use of potassium carbonate in a suitable aprotic solvent can be used. The resulting oxide (ii) may then contacted with compound (iii) (e.g., a 2-haloethanol or an alpha-halo omega hydroxyl polyoxyethylene compound of from 2 to 10 repeating oxyethylene groups), to form compound (iv), wherein q is as defined herein and Q is a halo group or leaving group (e.g., chloro, bromo, and iodo, or triflate, tosylate, and mesylate). Compounds such as, for example, commercially available (2-chloroethoxy)ethanol (Sigma Aldrich), 2-[(2-chloroethoxy)-2-(ethoxy)ethanol] (Sigma Aldrich), and the like may be used as compound (iii). The resulting product, (iv), can be recovered by conventional means and purified by crystallization, chromatography, precipitation, and the like. In some cases, the oxyalkylene chain of compound (iv) can be modified via the addition of a sugar or an oligosaccharide using standard procedures for generation of aglycons.

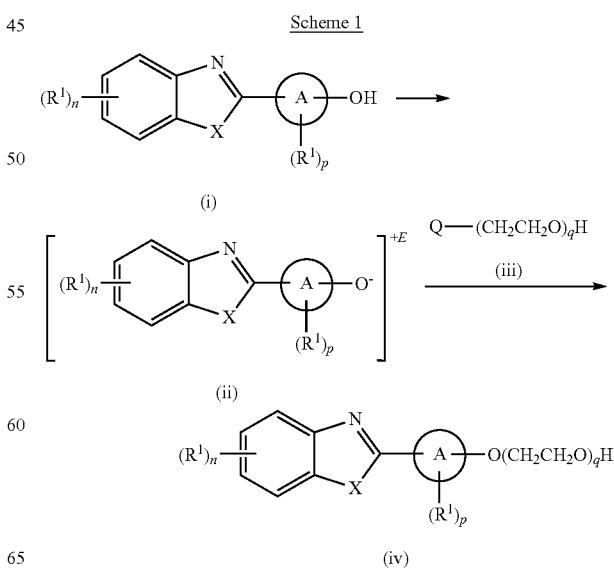

Scheme 1

Starting compound (i) may be obtained using known synthetic routes and commercially available starting reagents. For example, as shown below in Scheme 2, compound (i-a) can be produced from commercially available 2-bromobenzo[d]thiazole (i-c) and commercially available 6-bromopyridin-3-ol (i-b) under Suzuki coupling conditions. Compound (i-b), which can be optionally protected at the hydroxyl group), is converted to the corresponding boronic acid coupling partner, and subjected to conventional Suzuki conditions with (i-c) to provide for the 6-(benzo[d]thiazol-2-yl)pyridin-3-ol (i-a). The conditions for Suzuki reactions are replete in the literature.

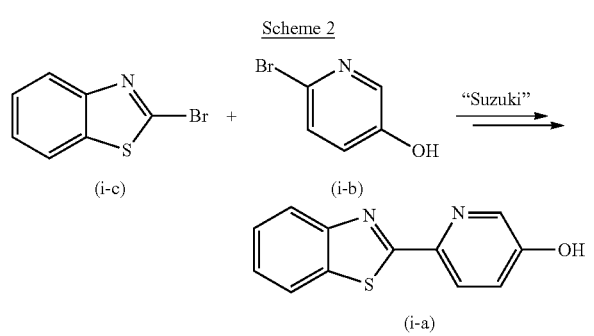

One of skill in the art will appreciate the synthetic methods and principles of chemical bonding for substitution of 1 or more $R^1$ groups, other than hydrogen, of compound (i) or compound (i-a). Alternatively, compounds of (i) and (i-a) having 1 or more $R^1$ substitutions other than hydrogen are commercially available. Other starting materials are well known and are commercially available, such as, for example, 2-bromobenzimidazole, 2-bromobenzoxazole, and substituted versions thereof. Compounds of Formula IA can be prepared similarly as compounds of Formula I, beginning with reagents such as, for example, 2-bromoindole, 2-bromobenzofuran, 2-bromobenzothiophene, and substituted versions thereof.

In some specific embodiments of the invention, compounds of Formula (VII) and Formula (VIIa) can be prepared by the following approaches, summarized in Scheme 3 and described below. As shown in Scheme 3, the direct condensation of o-aminothiophenol (i) with p-hydroxybenzaldehyde (ii), followed by an oxidative cyclization of the Schiff base intermediate to form the corresponding 2-substituted benzothiazole (iii), can be catalyzed by any suitable acidic reagent, wherein $R^1$, $R^2$, n and p are as defined herein for Formula (VII) and Formula (VIIa). For example, combining compounds (i) and (ii) in the presence of a suitable Lewis acid catalyst (e.g., $FeCl_3$, $ZrOCl_2$, $In(OTf)_3$, $Yb(OTf)_3$, or $Sc(OTf)_3$), under suitable conditions results in the corresponding 2-substituted benzothiazole (iii). The resulting benzothiazole (iii) may then contacted with compound (iv) (e.g., a 2-substituted polyethylene glycol compound), to form compound (v), wherein q is as defined herein and Q is a halo group or leaving group (e.g., chloro, bromo, and iodo, or triflate, tosylate, and mesylate). Compounds such as, for example, commercially available (2-chloroethoxy)ethanol (Sigma Aldrich), 2-[(2-chloroethoxy)-2-(ethoxy)ethanol] (Sigma Aldrich), and the like may be used as compound (iv). The resulting product, (v), can be recovered by conventional means and purified by crystallization, chromatography, precipitation, and the like.

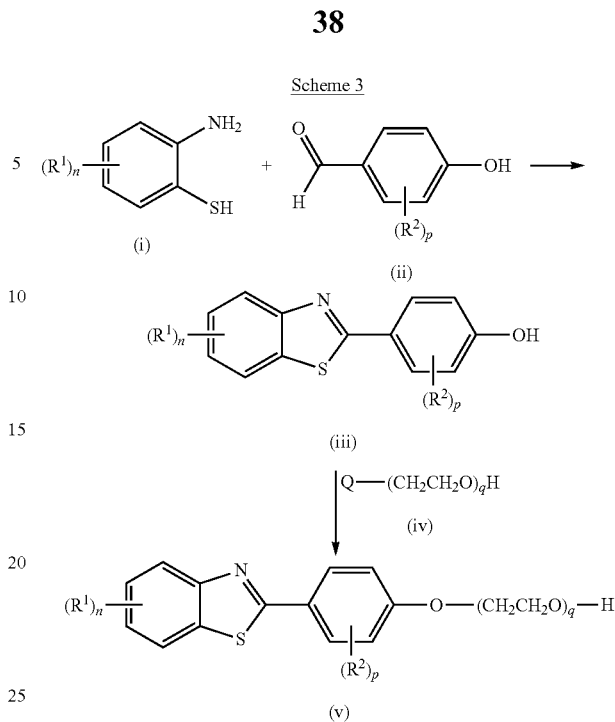

IV. PHARMACEUTICAL COMPOSITIONS

In another embodiment, the present invention provides a pharmaceutical composition, including a compound of the present invention described herein, or a pharmaceutically acceptable salt, solvate, and/or an N-oxide thereof, and one or more pharmaceutically acceptable excipients. Pharmaceutical compositions provided by the present invention include compositions wherein the active ingredient is a compound of Formula I, Formula IA, Formula II, Formula III, Formula IV, Formula V, Formula VI, Formula VII, and/or Formula VIIa, as described herein. In some embodiments, the pharmaceutical composition contains a compound of Formula (VII) or Formula (VIIa), or a pharmaceutically acceptable salt or solvate thereof.

The pharmaceutical compositions of the invention contain a therapeutically effective amount of the active ingredient. In some embodiments of the invention, a therapeutically effective amount of the active ingredient is an amount effective to achieve its intended purpose. In some embodiments of the invention, a therapeutically effective amount of the active ingredient can be an amount effective to increase dendritic spine density of neurons. In some embodiments of the invention, a therapeutically effective amount of the active ingredient can be an amount effective to decrease the neurotoxicity of beta-amyloid peptides to neurons. In some embodiments of the invention, a therapeutically effective amount of the active ingredient can be an amount effective to reduce the symptoms of traumatic brain injury.

The actual amount effective for a particular application can depend, inter alia, on the condition being treated (i.e., low dendritic spine density, beta-amyloid peptide neurotoxicity, traumatic brain injury). When administered in methods to treat a condition or disease (i.e., low dendritic spine density, beta-amyloid peptide neurotoxicity, traumatic brain injury) such compositions will contain an amount of active ingredient effective to achieve the desired result. Determination of a therapeutically effective amount of a compound of the invention is well within the capabilities of those skilled in the art, especially in light of the detailed disclosure herein.

Such compositions can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of the present invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable excipient and either a compound of the present invention, or a pharmaceutically acceptable salt of a compound of the present invention.

For preparing pharmaceutical compositions from the compounds of the present invention, pharmaceutically acceptable excipients can be either solid or liquid. Solid form preparations include powders, tablets, pills, capsules, cachets, suppositories, and dispersible granules. A solid excipient can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the excipient is a finely divided solid, which is in a mixture with a finely divided compound of the instant invention. In tablets, a compound of the instant invention is mixed with the excipient having the necessary binding properties in suitable proportions and compacted in the shape and size desired. The powders and tablets preferably contain from 5% or 10% to 70% of a compound of the instant invention.

The compositions typically include a conventional pharmaceutical excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of a compound of the present invention or a combination thereof, with the remainder consisting of suitable pharmaceutical excipients. Appropriate excipients can be tailored to the particular composition and route of administration by methods well known in the art, e.g., *REMINGTON'S PHARMACEUTICAL SCIENCES*, supra.

Suitable solid excipients include, but are not limited to, magnesium carbonate; magnesium stearate; calcium phosphate; calcium silicate; talc; pectin; dextran, dextrin, and cyclodextrin inclusion complexes; a low melting wax; cocoa butter; carbohydrates; sugars including, but not limited to, lactose, dextrose, sucrose, mannitol, or sorbitol; starches including, but not limited to, starch from corn, wheat, rice, potato, or other plants; cellulose such as methyl cellulose, hydroxypropylmethyl-cellulose, or sodium carboxymethyl-cellulose; and gums including arabic, tragacanth, and acacia; as well as proteins including, but not limited to, gelatin, collagen; microcrystalline cellulose, water, saline, syrup, ethylcellulose, and polyacrylic acids such as Carbopols, e.g., Carbopol 941, Carbopol 980, Carbopol 981, etc.; lubricating agents; mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents; biodegradable polymer beads. If desired, disintegrating or solubilizing agents may be added, such as the cross-linked polyvinyl pyrrolidone, agar, alginic acid, alginates, or a salt thereof, such as sodium alginate.

A pharmaceutically acceptable excipient may include physiologically acceptable compounds that act, for example, to stabilize the compounds of the present invention or modulate their absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable excipient, including a physiologically acceptable compound, depends, for example, on the route of administration of the compounds of the present invention and on the particular physiochemical characteristics of the compounds of the present invention.

Generally, such excipients should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and a compound of the instant invention is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving a compound of the instant invention in water and adding suitable colorants, flavors, stabilizers, and thickening agents as desired. Aqueous suspensions suitable for oral use can be made by dispersing the finely divided compound in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the compound of the instant invention, colorants, flavors, stabilizers, buffers, artificial and natural sweeteners, dispersants, thickeners, solubilizing agents, and the like.

Oil suspensions can be formulated by suspending a compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The following are representative pharmaceutical compositions containing a compound of the instant invention (i.e., active ingredient). For example, the active ingredient can be a compound of Formula (VII) or Formula (VIIa), or a pharmaceutically acceptable salt or solvate thereof. In some embodiments, the active ingredient can be a compound, or a pharmaceutically acceptable salt or solvate thereof, according to formula:

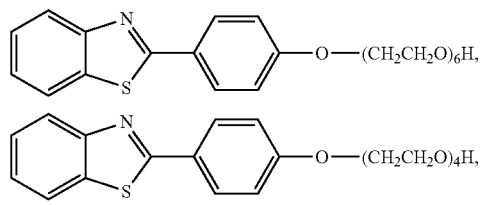

or a combination thereof.

The ingredients of Table 1 are mixed intimately and pressed into single scored tablets.

TABLE 1

Tablet formulation

| Ingredient | Quantity per tablet, mg |
|---|---|
| active ingredient | 400 |
| cornstarch | 50 |
| croscarmellose sodium | 25 |
| lactose | 120 |
| magnesium stearate | 5 |

The ingredients of Table 2 are mixed intimately and loaded into a hard-shell gelatin capsule.

TABLE 2

Capsule formulation

| Ingredient | Quantity per capsule, mg |
|---|---|
| active ingredient | 200 |
| lactose, spray-dried | 148 |
| magnesium stearate | 2 |

The ingredients of Table 3 are mixed to form a suspension for oral administration.

TABLE 3

Suspension formulation

| Ingredient | Amount |
|---|---|
| active ingredient | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 |
| flavoring | 0.035 mL |
| colorings | 0.5 mg |
| distilled water | q.s. to 100 mL |

The ingredients of Table 4 are mixed to form an injectable formulation.

TABLE 4

Injectable formulation

| Ingredient | Amount |
| --- | --- |
| active ingredient | 0.2-20 mg |
| sodium acetate buffer solution, 0.4M | 2.0 mL |
| HCl (1N) or NaOH (1N) | q.s. to suitable pH |
| water (distilled, sterile) | q.s. to 20 mL |

The ingredients of Table 5 are mixed to form a suppository having a total weight of, for example, 2.5 g. Witepsol® H-15 is a mixture of saturated vegetable fatty acid triglycerides, which is commercially available (e.g., Riches-Nelson, Inc., New York).

TABLE 5

Suppository formulation

| Ingredient | Amount |
| --- | --- |
| active ingredient | 500 mg |
| Witepsol ® H-15 | balance |

The dosage and frequency (single or multiple doses) of a therapeutically effective amount of the compounds described herein administered to a mammal can vary depending upon a variety of factors, for example, whether the mammal suffers from another condition or disease; its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of the present invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds' effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. In some embodiments, the dose of the compound administered to a patient can be effective or sufficient to increase dendritic spine density of neurons in the patient. In some embodiments, the dose of the compound administered to a patient can be effective or sufficient to decrease the neurotoxicity of beta-amyloid peptides to neurons in the patient. In some embodiments, the dose of the compound administered to a patient can be effective or sufficient to reduce the symptoms of traumatic brain injury in the patient. The size of the dose can be determined by the existence, nature, and extent of any adverse side-effects. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached.

Utilizing the teachings provided herein, an effective prophylactic or therapeutic treatment regimen can be planned that does not cause substantial toxicity and yet is effective to treat the clinical symptoms demonstrated by the particular patient. This planning can involve the careful choice of active compound by considering factors such as compound potency, relative bioavailability, patient body weight, presence and severity of adverse side effects, preferred mode of administration and the toxicity profile of the selected agent.

V. METHODS OF TREATMENT

Increasing Dendritic Spine Density and Decreasing β-Amyloid Peptide Neurotoxicity In some embodiments, the present invention provides a method for increasing dendritic spine density of neurons, which involves contacting the neurons with a therapeutically effective amount of a compound of the instant invention (i.e., a compound of Formula I, Formula IA, Formula II, Formula III, Formula IV, Formula V, Formula VI, Formula VII, and/or Formula VIIa) under conditions sufficient to increase dendritic spine density of neurons. In some embodiments, the present invention provides a method for increasing dendritic spine density of neurons, which involves contacting the neurons with a therapeutically effective amount of a compound of Formula VII and/or Formula VIIa, or a pharmaceutical composition thereof.

In one embodiment, the method for increasing dendritic spine density of neurons is conducted subsequent to a traumatic brain injury which puts a patient at risk of cognitive loss (either in the short term or long term). Such brain injuries include traumatic brain injuries well known in the art, as well as other repeated brain injuries, the cumulative effect of which is similar to a traumatic brain injury in that it places a patient at risk of cognitive loss (e.g., repeated concussions, transient ischemic events, and the like). Methods of diagnosing a patient with a traumatic brain injury, the methods of treating traumatic brain injuries using the compounds and compositions of the instant invention, as well as measuring the efficacy of treatments thereof, are described in more detail below.

It is recognized that dendritic spines act as sites of learning in memory in the brain. Song, et al., "A tetra (ethylene glycol) derivative of benzothiazole aniline ameliorates dendritic spine density and cognitive function in a mouse model of Alzheimer's disease" *Exp. Neuro.*, 252:105-113 (2014) which is incorporated herein by reference in its entirety. In addition, the art has shown that binding of small molecules to beta-amyloid inhibits formation of oligomers such as beta-sheets that neurotoxic. Still further, it is recognized that loss of spine density occurs in neurodegenerative diseases including Alzheimer's disease, Parkinson's disease and the like. As such, the methods of this invention provide a means to offset these loses and, therefore, mitigate the symptoms of such diseases.

In another embodiment, the present invention provides a method for decreasing the neurotoxicity of beta-amyloid peptides to neurons, which involves contacting the beta-amyloid peptides with a therapeutically effective amount of a compound of the instant invention (i.e., a compound of Formula I, Formula IA, Formula II, Formula III, Formula IV, Formula V, Formula VI, Formula VII, and/or Formula VIIa) under conditions sufficient to decrease the neurotoxicity of the beta-amyloid peptides. In some embodiments, the present invention provides a method for decreasing the neurotoxicity of beta-amyloid peptides to neurons, which involves contacting the beta-amyloid peptides with a therapeutically effective amount of a compound of Formula VII and/or Formula VIIa, or a pharmaceutical composition thereof. In some embodiments, the neurons are human neurons. In some embodiments, the compounds of the instant invention are suitable for treating diseases mediated by beta-amyloid as provided in detail above.

The compounds as described herein can be administered at any suitable dose in the methods of increasing dendritic spine density and/or decreasing beta-amyloid peptide neurotoxicity. In general, the compound is administered at a dose ranging from about 0.01 milligrams to about 1000 milligrams per kilogram of a subject's body weight (i.e., about 0.01-1000 mg/kg). The dose of the compound can be, for example, about 0.01-1000 mg/kg, or about 0.1-1000 mg/kg, or about 1-500 mg/kg, or about 25-250 mg/kg, or about 50-100 mg/kg. The dose of the compound can be about 0.5, 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. The dosages can be varied depending upon the requirements of the patient, the severity of the disorder being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the disease or condition.

The compounds can be administered for periods of time which will vary depending upon the nature of the particular disorder (i.e., low dendritic spine density, beta-amyloid peptide neurotoxicity), its severity, and the overall condition of the subject to whom the compound is administered. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a subject can be monitored for changes in his or her condition and for alleviation of the symptoms of the disorder. The dosage of the compound can either be increased in the event the subject does not respond significantly to a particular dosage level, or the dose can be decreased if an alleviation of the symptoms of the disorder is observed, or if the disorder has been remedied, or if unacceptable side effects are seen with a particular dosage.

A therapeutically effective amount of the compounds of the invention can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 144, 168, 192, 216, or 240 hours (i.e., 3, 4, 5, 6, 7, 8, 9, or 10 days). In certain embodiments, administration of one or more compounds of the invention is conducted in a chronic fashion over periods ranging from several months to several years. Accordingly, some embodiments of the invention provide a method of treating a disease or condition associated with low dendritic spine density or high amounts of neurotoxic beta-amyloid peptides (i.e., disorders associated with traumatic brain injury) as described herein, wherein the compound is administered to the subject for at least one year. In some embodiments, the compound is administered to the subject for at least 10 years. In some embodiments, the compound is administered to the subject for at least 60 years.

Assays to determine the effect of a candidate compound on dendritic spine expansion is set forth by Lee, et al., "Hexa(ethylene glycol) derivative of benzothiazole aniline promotes dendritic spine formation through the RasGRF1-Ras dependent pathway", *Biochimica et Biophysica Acta,* 1862 (2016):284-295 as well as by Megill, et al., Tetra (Ethylene Glycol) Derivative of Benzothiazole Aniline Enhances Ras-Mediated Spinogenesis", *Journal of Neurosciences,* 33(22)9306-9318 (2013) both of which are incorporated herein by reference in their entirety.

These protocols are illustrative of known methods for testing such candidate compounds and provides for dendritic spine expansion. Further, the compounds described herein are also useful in promoting cognitive function. Protocols for assessing such activity are provided by Song, et al., "A tetra(ethylene glycol) derivative of benzothiazole aniline ameliorates dendritic spine density and cognitive function in a mouse model of Alzheimer's disease" *Exp. Neuro.,* 252: 105-113 (2014), which incorporated herein by reference in its entirety.

In addition, in mammalian systems, fascin, an actin-bundling protein (~55 kD), increases cell motility in multiple human malignancies. Hwang, et al., Neoplasia, 2008 (10)2:149-159. Indeed, fascin has been shown to down-regulate the expression and nuclear translocation of a key metastasis suppressor protein known as breast cancer metastasis suppressor-1 (BRMS1). In addition, fascin up-regulates NF-kappa B activity, which is essential for metastasis. Importantly, fascin up-regulates other proteins that are known to be critical for the execution of metastasis such as urokinase-type plasminogen activator (uPA) and the matrix metalloproteases (MMP)-2 and MMP-9. Al-Awan, et al., PLoS One. 2011; 6(11):e27339. doi: 10.1371/journal-.pone.0027339. Epub 2011 Nov. 4.

The compounds of this invention are designed to bind to fascin and, as such, to mitigate its activity and, thus, reduce tumor metastasis. Therefore, the compounds of this invention are useful in mitigating metastases of tumors. In such methods, the compounds are administered, preferably as a pharmaceutical composition, in an effective amount as described above. In normal adult tissues, fascin is expressed in neurons and dendritic cells. This suggests a neurological role for fascin. As the compounds described herein bind fascin, such binding can play a critical role in understanding such neurological roles and how binding modulates those roles.

Accordingly, in one aspect, there is provided a method for modulating the activity of fascin by complexing fascin to a compound of this invention. In one further embodiment, such modulation includes mitigating the metastatic properties of fascin. In another further embodiment, such modulation includes up regulating or down regulating the neurological properties of fascin. Still further, in another embodiment, there is provided a complex of fascin with one or more molecules of Formula I, Formula IA, Formula II, Formula III, Formula IV, Formula V, Formula VI, Formula VII, and/or Formula VIIa as described herein. It is contemplated that such a complex will contain any appropriate binding interactions such as ionic interactions, hydrophilic/hydrophobic interactions, and where possible covalent binding.

Methods of Reducing TBI Symptoms

In some embodiments, the present invention provides a method for reducing the symptoms of traumatic brain injury in a patient suffering from traumatic brain injury by administering a therapeutically effective amount of a compound of the invention (i.e., a compound of Formula I, Formula IA, Formula II, Formula III, Formula IV, Formula V, Formula VI, Formula VII, and/or Formula VIIa), or a pharmaceutically acceptable salt or solvate thereof, wherein the therapeutically effective amount of the compound, or pharmaceutically acceptable salt or solvate thereof, is an amount sufficient to reduce the symptoms of traumatic brain injury. In some embodiments, the present invention provides a method for reducing the symptoms of traumatic brain injury in a patient, which involves administering a therapeutically effective amount of a compound of Formula VII and/or Formula VIIa, or a pharmaceutical composition thereof.

Traumatic brain injury may occur as a result of a head injury. A head injury can include any of the following: a bump to the head, a blow to the head, a jolt to the head, a sudden acceleration, a sudden deceleration, a sudden twisting of the head, a compression of the brain as a result of a nearby explosion or a penetrating head injury, and/or any type of force applied to the head which disrupts the normal function of the brain. In some embodiments of the invention, a TBI can be the result of a head injury, wherein the head injury can be caused by, for example, blunt trauma to the head or a blow to the head.

In some embodiments of the invention, a traumatic brain injury can be a mild, moderate, or severe traumatic brain injury. In other embodiments, a TBI can be a mild TBI (mTBI). In some embodiments, the mildest form of TBI (mTBI) can also be called a concussion, and is characterized by a temporary loss of brain function. As an example, a concussed patient can temporarily lose consciousness from a few seconds up to 30 minutes. When assessing whether or not a patient should receive treatment for a traumatic brain injury (i.e., treatment for the reduction in the symptoms of traumatic brain injury), it is necessary to confirm whether or not the patient has acquired a traumatic brain injury. Described herein are several methods and assessments that can be used to diagnostically determine the initial and subsequent level of neurologic damage of a patient with TBI.

In some embodiments of the invention, a patient having experienced a head injury can be diagnosed as having a mTBI by observing the patient and subsequently recognizing that the patient is experiencing symptoms of a traumatic brain injury. For example, a patient having a head injury can be diagnosed as having a mTBI if the patient experiences one or more of the following conditions: (1) observed or self-reported contusion, disorientation, or impaired consciousness, dysfunction of memory at the time of the injury, loss of consciousness lasting less than 30 minutes; and, (2) symptoms such as headache, dizziness, fatigue, irritability, impaired memory and poor concentration soon after the injury.

In other embodiments of the invention, a patient having a head injury can be diagnosed as having a TBI by evaluating the severity of the head injury using a test or a combination of tests. For example, a patient can be diagnosed as having a TBI by using the Glasgow Coma Scale (GCS). The GCS is an assessment that can measure and score the eye opening, verbal, and motor responses of a patient that has experienced a head injury. The GCS score is the sum total score of each measured response. A GCS score may increase or decrease over time. The general definition of the scores is Severe (3-8), Moderate (9-12) and Mild (13-15). The GCS can be implemented to evaluate the response of patients having experienced a serious traumatic brain injury (i.e., unconscious patients). The Glasgow Coma Scale is a commonly used method of diagnosing traumatic brain injuries in patients and is known to those skilled in the art (http://www.glasgowcomascale.org).

In some embodiments of the invention, a patient having a head injury can be diagnosed as having a TBI using the Rivermead Post-Concussion Questionnaire (RPQ). The RPQ is useful in determining the severity of several symptoms and functional deficits in a patient having been observed as having a concussion (mTBI). Patients can be asked to rate the severity of symptoms that they experience. The symptoms that are evaluated using the RPQ include: headaches, dizziness, nausea and/or vomiting, hyperacusis, sleep disturbance, fatigue, blurred vision, double vision, light sensitivity, restlessness, irritability, frustration, depression, memory loss, poor concentration, and taking a longer time to think. These symptoms can be evaluated within 24 hours of a patient having experienced a head injury. The RPQ is a commonly used method of diagnosing traumatic brain injuries in patients and is known to those skilled in the art (King, N.; Crawford, S.; Wenden, F.; Moss, N.; and Wade, D. (1995) *Journal of Neurology* 242: 587-592).

Several other tests used to diagnose a patient with a TBI include: Military Acute Concussion Evaluation (MACE) (Kennedy, C. H.; Moore, J. L. *Military Neuropsychology* (2010); Immediate Post-Concussion Assessment and Cognitive Test (ImPACT) (https://www.impacttest.com); Sports Concussion Assessment Tool (SCAT) (http://physicians.cattonline.com/scat/); Automated Neuropsychological Assessment Metrics (ANAM) (*Archives of Clinical Neuropsychology* (2007), 22, Suppl. 1, S1-S144); and Cogstate (https://cogstate.com). The assessments described herein are commonly used methods to diagnose patients with a TBI and are known to those skilled in the art.

A patient can be diagnosed as having a traumatic brain injury by monitoring the level of particular biomarkers in the patient's blood. Specifically, the glial fibrillary acidic protein (GFAP) and ubiquitin C-terminal hydrolase L1 (UCH-L1) are the biomarkers that can be measured at multiple time points in patients with mild to moderate TBI (i.e., a GCS 9-15). The blood test results measuring the levels of GFAP and UCH-L1 in the patients at multiple time points indicate whether or not a TBI has occurred. For example, the levels of GFAP and UCH-L1 are both elevated very soon after a TBI, but then decline within a week to substantially lower levels. It is known to one skilled in the art how to diagnose a TBI using biomarkers (Papa, L. *JAMA Neurol.* (2016) 73 (5), 551-560).

In some cases, a patient can be diagnosed as having a traumatic brain injury using methods of neuroimaging, such as computerized axial tomography (CAT or CT) and magnetic resonance imaging (MRI). CT and MRI scans can be used to identify the severity of a brain injury. For example CT and MRI scans are often used in hospitals to identify brain injuries, though they are often not useful at detecting mTBI in which there is no obvious damage to the brain. In some embodiments, patients having a mTBI with a normal CT or MRI scan can be distinguished from patients having a moderate TBI with bleeding in the brain and an abnormal CT or MRI scan. A CT scan may be implemented within the first 24 hours of a brain injury, and can be useful at detecting bony pathology and some types of early brain bleeds. An MRI scan is considered more valuable when performed 48 to 72 hours after a brain injury, and can be useful at hemorrhagic cortical contusions, petechiae, axonal injury, and subtle neuronal damage. In general, the methods of neuroimaging can be most useful to patients having experienced a moderate to serious traumatic brain injury. It is known to one skilled in the art how to diagnose a TBI using neuroimaging methods (Lee, B. *NeuroRX* (2005) 2 (2), 372-383; International application number PCT/US2015/024739).

In some embodiments of the invention, a patient can be diagnosed as having a traumatic brain injury by any one of the methods described above or known in the art, or any combination of the methods described above or known in the art. In other embodiments, the patient having a head injury is diagnosed with a TBI by observation and recognition of TBI symptoms, in addition to implementing an assessment, such as the GCS or the RPQ. In other embodiments, the patient having a head injury is diagnosed with a TBI by observation and recognition of TBI symptoms, in addition to monitoring biomarkers. In other embodiments, the patient having a head injury is diagnosed with a TBI using multiple assessments, such as the GCS, RPQ, and MACE. In other embodiments, the patient having a head injury is diagnosed with a TBI using neuroimaging methods, in addition to monitoring biomarkers and performing an assessment, such as the GCS or the RPQ. In other embodiments, the patient having a head injury is diagnosed with a TBI using neuroimaging methods, in addition to monitoring biomarkers. In other embodiments, the patient having a head injury is diagnosed with a TBI using neuroimaging methods, in addition to performing an assessment, such as the GCS or the RPQ. In some other embodiments, the patient having a head injury is diagnosed with a TBI using neuroimaging methods, such as MRI and CT scans. In some embodiments, the patient having a head injury is diagnosed with a TBI by monitoring the levels of biomarkers. In other embodiments, the patient having a head injury is diagnosed with a TBI by observation and recognition of TBI symptoms. In other embodiments, the patient having a head injury is diagnosed with a TBI using one assessment, such as the GCS or RPQ. In some embodiments, the patient having a head injury is diagnosed with a TBI using the RPQ assessment.

In further embodiments of the invention, a patient having a head injury is diagnosed with a TBI using any of the methods and assessments described herein immediately after receiving the head injury, i.e. within 0 hours of receiving a head injury. In some embodiments, the patient having a head injury is diagnosed with a TBI within about 5 minutes, 10 minutes, 15 minutes, 20 minutes, 30 minutes, 45 minutes, 1 hour, 4 hours, 12 hours, 18 hours, 24 hours, 30 hours, 36 hours, 42 hours or 48 hours of receiving a head injury. In some embodiments, a patient having a head injury is diagnosed with a TBI within about 0 to about 48 hours of receiving a head injury, or about 5 minutes to about 42 hours, or about 10 minutes to about 36 hours, or about 15 minutes to about 30 hours, or about 20 minutes to about 24 hours, or about 30 minutes to about 18 hours, or about 45 minutes to about 12 hours, or about 1 to about 4 hours of receiving a head injury. In some embodiments, a patient having a head injury is diagnosed with a TBI within about 0 hours to about 1 hour of receiving a head injury. In another embodiment, a patient having a head injury is diagnosed with a TBI within about 30 minutes of receiving a head injury.

In some cases, patients diagnosed with a concussion/mTBI and more serious TBIs can experience neurological effects caused by altered levels of neurochemicals, and subsequent neuron damage. The neurological effects can linger for days, weeks, months or years. These neurological effects cause deficits in the following functional domains: physical, visual, auditory, neurobehavioral, cognitive-communication, and sleep. Deficits of the physical domain can induce any of the following symptoms: nausea, vomiting, dizziness, headaches, seizures, changes in consciousness, fatigue, weakened muscles, impaired balance, and/or impaired coordination. Deficits of the visual domain can induce any of the following symptoms: light sensitivity, double vision, decreased visual acuity, visual neglect, and/or changes in the accommodation-convergence reflex. Deficits of the auditory domain can induce any of the following symptoms: hyperacusis, tinnitus, hearing loss, and/or central auditory dysfunction. Deficits of the neurobehavioral domain can induce any of the following symptoms: agitation, anxiety, depression, mood swings, restlessness, disorientation, impulsivity, irritability, impatience, and/or stress disorders Deficits of the cognitive-communication domain can induce any of the following symptoms: attention deficits, executive function deficits, information processing impairments, memory deficits, learning deficits, impaired metacognition, impaired spatial cognition, aphasia, and/or motor speech deficits. Deficits of the sleep domain can induce any of the following symptoms: insomnia, hypersomnia, and/or sleep disturbance.

In some embodiments, a patient diagnosed with a TBI can have a deficit in one or more functional domains. A patient diagnosed with a TBI having a deficit in one or more functional domains can receive a therapeutically effective amount of a compound of the invention (i.e., a compound of Formula I, Formula IA, Formula II, Formula III, Formula IV, Formula V, Formula VI, Formula VII, and/or Formula VIIa). In some embodiments, a patient diagnosed with a TBI having a deficit in one or more functional domains can receive a therapeutically effective amount of a compound of Formula VII and/or Formula VIIa, or a pharmaceutical composition thereof. For example, a patient diagnosed with a TBI having a deficit in one or more functional domains can receive a therapeutically effective amount of a compound, or pharmaceutically acceptable salt or solvate thereof, according to formula:

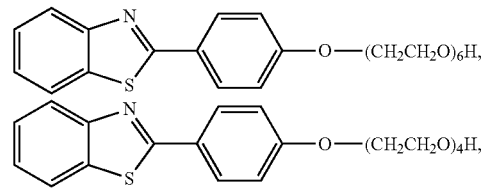

or a combination thereof.

Dosage amounts and intervals can be adjusted individually to provide levels of the administered compound effective for the particular clinical indication being treated. This will provide a therapeutic regimen that is commensurate with the severity of the traumatic brain injury and state of the patient.

In some embodiments, suitable dosage ranges for the active agent (i.e. a compound described herein) include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the active agent include about 1 mg, 5, 10, 20, 30, 40, 50, 60, 70, 80, 90, 100, 200, 300, 400, 500, 600, 700, 800, 900 or 1200 mg.

In some embodiments, the dosage of a pharmaceutical composition for oral administration of a compound described herein can be about 0.1 mg/kg of body weight per patient, or 0.5, 1, 5, 10, 25, 50, 100, 250, 500, 750, or 1000 mg/kg of body weight per patient. In other embodiments, the dosage of a pharmaceutical composition for oral administration of a compound described herein can be from about 0.1 to 1000 mg/kg of body weight per patient, or from about 0.5 to 750, or from about 1 to 500, or from about 5 to 250, or from about 10 to 100, or from about 25 to 50 mg/kg of body weight per patient. In still another embodiment, the dosage can be between about 0.5 to about 25 mg/kg of body weight per patient, or between about 5 to 15 mg/kg of body weight per patient, or between about 8 to about 12 mg/kg of body weight per patient, or about 10 mg/kg of body weight per patient. Lower dosages can be used, particularly when the drug is administered to an anatomically secluded site, such as the cerebral spinal fluid (CSF) space, in contrast to administration orally, into the blood stream, into a body cavity or into a lumen of an organ. Actual methods for preparing parenterally administrable compound formulations will be known or apparent to those skilled in the art and are described in more detail in such publications as Remington's, supra. See also Nieman, In "Receptor Mediated Antisteroid Action," Agarwal, et al., eds., De Gruyter, New York, 1987.

The active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w).

In certain embodiments of the invention, a patient having been diagnosed with a TBI can be administered a therapeutically effective amount of a compound (including embodiments, examples, and/or pharmaceutical compositions thereof) in a dosage described above immediately after receiving the TBI, i.e. within 0 hours of receiving the TBI. In some embodiments, the patient having a TBI can be administered a therapeutically effective amount of a compound within about 10 minutes of receiving the TBI, or within about 20 minutes, 30 minutes, 45 minutes, 1 hour, 2 hours, 4 hours, 7 hours, 12 hours, 18 hours, 24 hours, 30 hours, 36 hours, 48 hours, or 72 hours of receiving the TBI. In some embodiments, a patient having a TBI can be administered a therapeutically effective amount of a compound within about 0 to about 72 hours of receiving the TBI, or within about 10 minutes to about 48 hours, or within about 20 minutes to about 36 hours, or within about 30 minutes to about 30 hours, or within about 45 minutes to about 24 hours, or within about 1 to about 18 hours, or within about 2 to about 12 hours, or within about 4 to about 7 hours of receiving the TBI. In certain other embodiments of the invention, a patient having a TBI can be administered a therapeutically effective amount of a compound within about 0 to 24 hours of receiving the TBI. In other embodiments of the invention, a patient having a TBI can be administered a therapeutically effective amount of a compound within about 18 hours of receiving the TBI. In other embodiments of the invention, a patient having a TBI can be administered a therapeutically effective amount of a compound within no more than 18 hours of receiving the TBI. In certain embodiments of the invention, a patient having a TBI can be administered a therapeutically effective amount of a compound within 4 hours of receiving the TBI. In some other certain embodiments of the invention, a patient having a TBI can be administered a therapeutically effective amount of a compound within 1 hour of receiving the TBI.

In some embodiments of the invention, a patient having a TBI can be administered a therapeutically effect amount in a dosage described above of a compound (including embodiments, examples, and/or pharmaceutical compositions thereof) at least once per 30 minutes, or 1 hour, 2 hours, 3 hours, 4 hours, 6, hours, 8 hours, 12 hours, 18 hours, or 24 hours. In other embodiments, a patient having a TBI is administered a dose of a pharmaceutical composition of a compound at least once per 30 minutes to 24 hours, or at least once per 1 hour to 18 hours, or at least once per 2 to 12 hours, or at least once per 3 to 8 hours, or at least once per 4 to 6 hours.

In some embodiments of the invention, a patient having a TBI can receive a treatment regimen as described above (i.e. dosage and dosage frequency of a therapeutically effective amount of a compound of Formula (VII) or Formula (VIIa)) for any suitable length of time. In other embodiments, a patient having a TBI can receive a treatment regimen for about 1 day, or 2, 3, 5, 7, 10, 14, 20, 25, 30, 35, 45, 60, or about 90 days. In some embodiments, a patient having a TBI can receive a treatment regimen for about 1 day to about 90 days, or about 2 to about 60, or about 3 to about 45, or about 5 to about 35, or about 7 to about 30, or about 10 to about 25, or about 14 to about 20 days. In another embodiment, a patient having a TBI can receive a treatment regimen for about 35 days.

VI. Measuring Tbi Treatment Efficacy

A patient diagnosed with a traumatic brain injury who has received treatment for reducing the symptoms of the traumatic brain injury as described above (i.e., a patient being administered a therapeutically effective amount of a compound) will be evaluated periodically throughout the patient's treatment regimen to determine the treatment's efficacy. A patient being administered a therapeutically effective amount of compound can be evaluated for an improvement in the performance of one or more functional domains (i.e., physical, visual, auditory, neurobehavioral, cognitive-communication, and sleep). In some embodiments, a patient being treated for a TBI can be evaluated for an improvement in one or more of the functional domains using any one of the methods used to diagnose the patient with a TBI (as described herein or known in the art), or any combination of such methods. For example, a TBI patient receiving a treatment regimen described above can be evaluated for an improvement in one or more of the functional domains by monitoring the level of GFAP and UCH-L1 biomarkers in the patient's blood and/or using any of the following assessments: GCS, RPQ, MACE, ImPACT, SCAT, ANAM, and/or Cogstate. In some embodiments of the invention, a TBI patient receiving a treatment regimen can be evaluated for an improvement in one or more of the functional domains using GCS, RPQ, and/or MACE. In other embodiments of the invention, a TBI patient receiving a treatment regimen can be evaluated for an improvement in one or more of the functional domains using GCS and RPQ. In certain embodiments of the invention, TBI patient receiving a treatment regimen can be evaluated for an improvement in one or more of the functional domains using RPQ.

In certain embodiments of the invention, a TBI patient receiving treatment can be evaluated for an improvement in the performance of one or more functional domains for any suitable number of times during the span of a TBI treatment regimen. In some embodiments of the invention, a TBI patient receiving treatment can be evaluated for an improvement in the performance of one or more functional domains at least 1 time per treatment regimen, or about 2, 3, 6, 12, 15, 18, 20, 25, 30, 40, 50, 60, 80, 100, or 150 times per treatment regimen. In other embodiments of the invention, a TBI patient receiving treatment can be evaluated for an improvement in the performance of one or more functional domains about 1 to about 150 times per treatment regimen, or about 2 to about 100, or about 3 to about 80, or about 6 to about 60, or about 12 to about 50, or about 15 to about 40, or about 18 to about 30, or about 20 to about 25 times per treatment regimen. In certain embodiments, a TBI patient receiving treatment can be evaluated for an improvement in the performance of one or more functional domains about 3 to about 80 times per treatment regimen. For example, a TBI patient receiving a treatment regimen for about 35 days can be evaluated for an improvement in the performance of one or more functional domains anywhere between 3 and 80 times during the 35 day span of treatment regimen.

In embodiments of the invention, the reduction of the symptoms of traumatic brain injury in a TBI patient can be observed as an improvement in the performance of one or more functional domains in the TBI patient. Alternatively, an improvement in the performance of one or more functional domains in a TBI patient can be observed as a reduction of the symptoms of traumatic brain injury in the TBI patient.

After receiving treatment for a TBI, the measured performance of one or more functional domains in a patient will improve by a percentage (%) compared to the performance of the one or more functional domains measured prior to treatment but after injury. In some embodiments of the invention, the performance of one or more functional domains can improve by at least 1% compared to the performance of the one or more functional domains measured prior to treatment but after injury, or by at least 5, 10, 15, 20, 25, 30, 35, 40, 50, 60, 70 or 80% compared to the performance of the one or more functional domains measured prior to treatment but after injury. In other embodiments, the measured performance of one or more functional domains in a patient can improve by at least 1% to 80% compared to the performance of the one or more functional domains measured prior to treatment but after injury, or by at least 1% to 80%, or by at least 5% to 70%, or by at least 10% to 60%, or by at least 15% to 50%, or by at least 20% to 40%, or by at least 25% to 35% compared to the performance of the one or more functional domains measured prior to treatment but after injury. In certain embodiments, the performance of one or more functional domains can improve by at least 20% to 30% compared to the performance of the one or more functional domains measured prior to treatment but after injury.

In some embodiments of the invention, the performance of one or more functional domains can improve within any suitable amount of time of treatment. In other embodiments, the performance of one or more functional domains can improve within about 24 hours of treatment, or within about 48 hours, 72 hours, 5 days, 7 days, 14 days, 4 weeks, 6 weeks, 8 weeks, 12 weeks, 16 weeks, or 20 weeks of treatment. In some embodiments of the invention, the performance of one or more functional domains can improve within about 24 hours to about 20 weeks of treatment, or within about 48 hours to about 16 weeks, or within about 72 hours to about 12 weeks, or within about 5 days to about 8 weeks, or within about 7 days to about 6 weeks, or within about 14 days to about 4 weeks of treatment. In certain embodiments, the performance of one or more functional domains can improve within about 7 days to about 4 weeks of treatment. In other particular embodiments, the performance of one or more functional domains can improve within about 7 days of treatment.

VII. EXAMPLES

The following examples are offered to illustrate, but not to limit the claimed invention.

Example 1. Synthesis of 2-(2-(2-(2-(4-(benzo[d]thiazol-2-yl)phenoxy)ethoxy)ethoxy) ethoxy)ethan-1-ol (3, "Benzothiazole-IIIB")

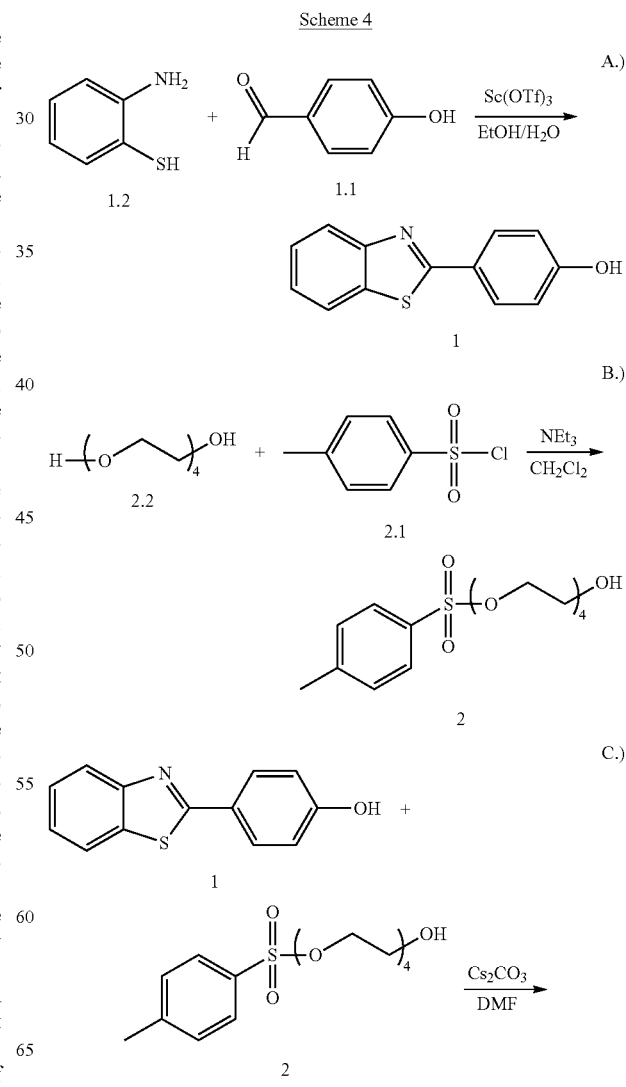

-continued

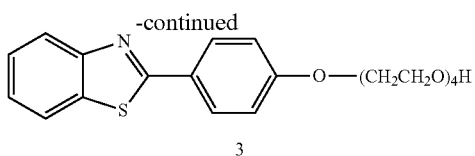

3

Step A.): Preparation of 4-(benzo[d]thiazol-2-yl)phenol (1). All reagents were obtained from Sigma Aldrich and used as such. To 40 mL of a 1:1 ethanol/water solvent mixture was added scandium triflate (Sc(OTf)$_3$, 1 g, 2 mmol), 2-aminobenzenethiol (1.2, 3.6 g, 28.8 mmol), and 4-hydroxybenzaldehyde (1.1, 3.6 g, 29.5 mmol). The reaction mixture was stirred at 50° C. overnight in an open flask. After completion of the oxidation reaction, the reaction was cooled to room temperature (r.t.) and filtered. The isolated solids were washed with ether and dried, producing 4-(benzo[d]thiazol-2-yl)phenol (1) in a 70-80% yield.

Step B.): Preparation of tetraethylene glycol p-toluenesulfonate (2). All reagents were obtained from Sigma Aldrich and used as such. To a solution of tetraethylene glycol (2.2, 3.88 g, 20 mmol) in 100 mL of dichloromethane was added tosyl chloride (2.1, 3.8 g, 20 mmol). The reaction mixture was then cooled to −78° C. before slowly adding triethylamine (2.01 g, 20 mM) dropwise and stirred overnight. The reaction mixture was allowed to slowly warm to r.t. before washing with 1 L of water and drying to afford the crude product. Pure tetraethylene glycol p-toluenesulfonate (2) was isolated in a 40-50% yield after purification using an ISCO CombiFlash 80 g silica cartridge and 0-100% ethyl acetate/hexane.

Step C.): Preparation of 2-(2-(2-(2-(4-(benzo[d]thiazol-2-yl)phenoxy)ethoxy) ethoxy)ethan-1-ol (3). All reagents were obtained from Sigma Aldrich and used as such. To a solution of 1 (2.27 g, 10 mmol) in 30 mL DMF was added cesium carbonate (3.26 g, 10 mmol), and 2 (4.05 g, 11.6 mmol). The reaction mixture was stirred overnight at 60° C. The reaction mixture was then cooled down to r.t. before washing with 1 L of a 1:1 water/ethyl acetate solvent mixture and drying to afford the crude product. Pure 2424242-(4-(benzo[d]thiazol-2-yl)phenoxy)ethoxy)ethoxy) ethoxy)ethan-1-ol (3) was obtained using an ISCO Combi-Flash and 0-100% dichloromethane/ethyl acetate. Pure fractions were combined, dried, washed with ether, filtered, and dried again to yield 4 g of 3 (72% yield). Purity was determined by HPLC 0-100% acetonitrile/water containing 1 g per liter ammonium acetate. $^1$H NMR (600 MHz, DMSO-d6): δ 8.15 (d, 1H), 8.05-8.15 (m, 3H), 7.6 (d, 1H), 7.4 (d, 1H), 7.1 (d, 2H), 4.6 (m, 1H), 4.25 (m, 2H), 3.3-3.8 (m, 14H). APCI (LCQ): m/z [M+H]$^+$ calcd for $C_{21}H_{25}NO_5S$, 403.49; found, 404.1.

Example 2. In Vitro Spinogenesis Using Benzothiazole Compounds

Compounds of the current invention bind to the actin bundling protein, fascin, and prevent the formation of long, stiff actin cytoskeleton, thereby promoting dendritic spine formation. (see, Sedeh, R. S. et al. *J. Mol. Biol.* 400, 589-604 (2010); Chen, L. et al. *Nature* 464, 1062-1066 (2010); Jansen, S. et al. *J. Biol. Chem.* 286, 30087-30096 (2011); Yang, S. et al. *J. Biol. Chem.* 288, 274-284 (2013); Zheng, S. et al. *J. Med. Chem.* 57, 6653-6667 (2014)). To demonstrate the efficacy of the compounds of this invention for promoting spinogenesis, the effect of the benzothiazole compounds on synaptic puncta and synapses of mouse cortical neurons was investigated. Specifically, the Benzothiazole-IIIA and Benzothiazole-IIIB compounds of the instant invention, as well as the Benzothiazole-I compound as described in International application number PCT/US2017/012139, were used in this study (FIG. 1).

Figure 2:
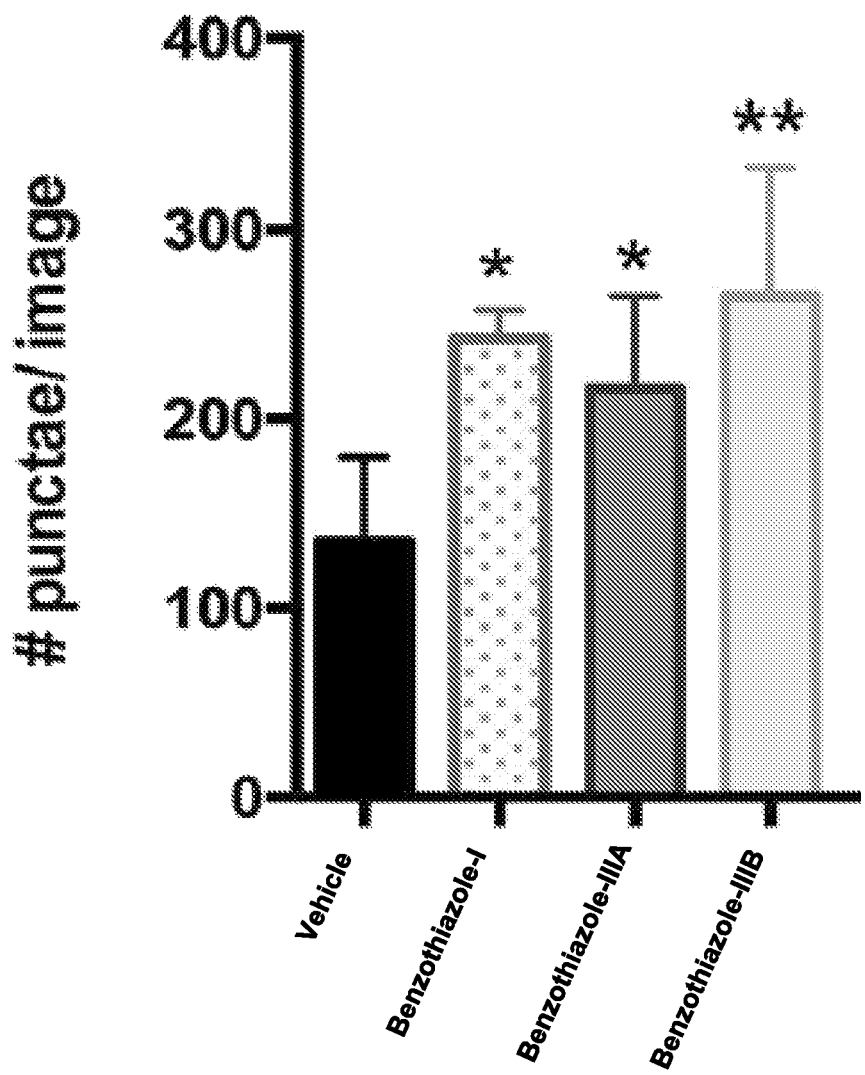
FIG. 2. The effect of benzothiazole compounds (5 µM) on the number of puncta from primary mouse cortical neurons (DIV 16) after 24 hours of treatment starting at DIV 15. * $p<0.05$, ** $p<0.01$.

Primary mouse cortical neurons were treated with 5 µM of Benzothiazole-I, Benzothiazole-IIIA, or Benzothiazole-IIIB at DIV 15. As a control, primary mouse cortical neurons were treated with the vehicle only (10% DMSO, 90% phosphate buffered saline (PBS)). After 24 hours, the DIV 16 neurons were fixed, immunostained using the presynaptic vesicle protein synaptophysin (P38), counterstained with the nuclear dye DAPI (4',6-diamidino-2-phenylindole,), and counted. Immunolabeled neurons were imaged on a Leica confocal microscope. The numbers of P38-immunopositive puncta were analyzed using FIJI with the Squash plugin (FIG. 2). As shown in FIG. 2, Benzothiazole-I, Benzothiazole-IIIA, and Benzothiazole-IIIB all cause an increase in the number of synaptic puncta compared to the vehicle control.

Figure 3:
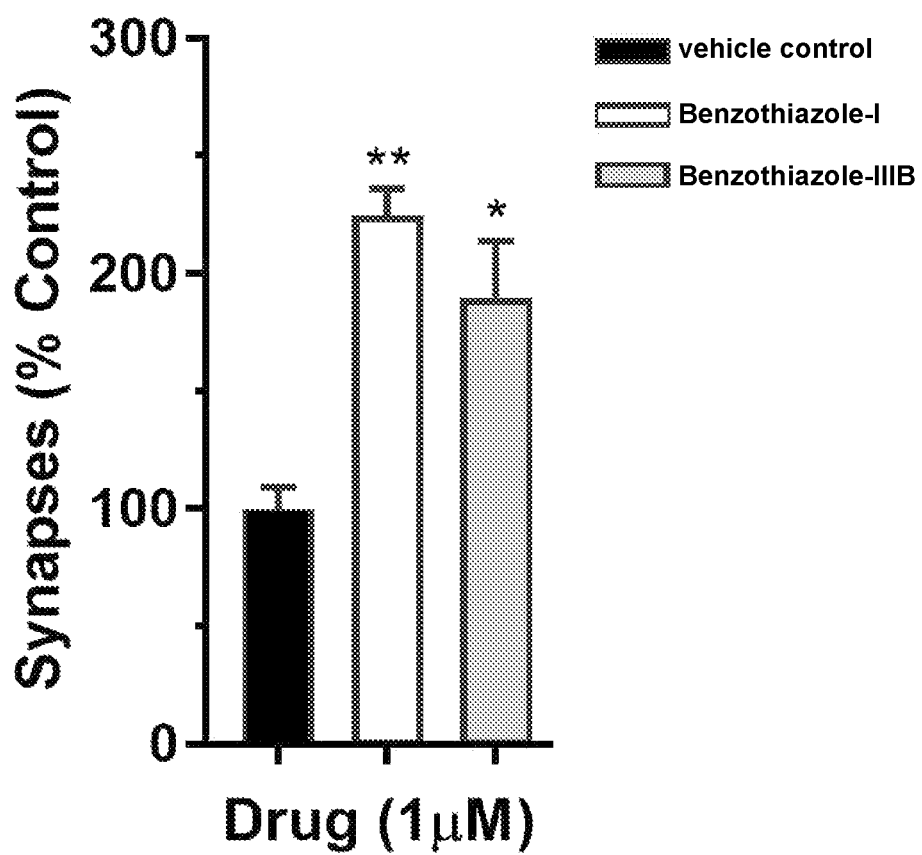
FIG. 3. The effect of benzothiazole compounds (1 µM) on the synaptic density from primary mouse cortical neurons (DIV 16) after 24 hours of treatment starting at DIV 15. * $p<0.05$, ** $p<0.01$.

In a similar experiment, the primary mouse cortical neurons were treated with 1 µM of Benzothiazole-I or Benzothiazole-IIIB at DIV 15, using the same DMSO/PBS buffer solution described above as the control vehicle. After 24 hours, the DIV 16 neurons were fixed, immunolabeled with synaptophysin, stained with DAPI, and counted as described above. FIG. 3 shows that after 24 hrs, Benzothiazole-I and Benzothiazole-IIIB promote about a 100% increase in the number of synapses when compared to the control.

Example 3. In Silico Fascin Binding of Benzothiazole Compounds

In order to evaluate the ability of the benzothiazole compounds to bind to fascin and thereby inhibit the formation of bundled actin fibrils, an in silico study was carried out using benzothiazole compounds and available crystal structures of Human Fascin 1. Binding sites were identified on the surface of each fascin crystal structure, followed by virtual docking of Benzothiazole-I, Benzothiazole-II, Benzothiazole-IIIA, and Benzothiazole-IIIB (FIG. 1) in each pocket to determine favorable binding conformations.

Analysis and Preparation of Fascin Crystal Structures

All available Fascin crystal structures were downloaded from the PDB and prepared for structure analysis (see, Sedeh, R. S. et al. *J. Mol. Biol.* 400, 589-604 (2010); Chen, L. et al. *Nature* 464, 1062-1066 (2010); Jansen, S. et al. *J. Biol. Chem.* 286, 30087-30096 (2011); Yang, S. et al. *J. Biol. Chem.* 288, 274-284 (2013)). The structures were analyzed by eye and by standard automated protocols embedded in MolSoft's ICM-Pro software. Hydrogen atoms were added to the structures, and considerations were made regarding: correct orientation of Asn and Gln side-chains, ligand and protein charges, histidines orientation and protonation state, and any crystallographic quality flags, such as high b-factors or low occupancy.

Pocket Identification

MolSoft's ICMPocketFinder algorithm was used to identify potential ligand binding pockets and cavities in all the available Fascin crystal structures (see, An, J., et al. *Genome Inform. Int. Conf. Genome Inform.* 15, 31-41 (2004); Kufareva, I., et al. *Nucleic Acids Res.* 40, D535-540 (2012)). First, pockets in the active chain A of crystal structure 3LLP were searched, as this structure had the highest resolution (1.8 Å). Four "drug-like" pockets were identified as having properties suitable for binding small molecules (FIG. 4).

Ligand Docking and Scoring

The head groups and head+tail of Benzothiazole-I, Benzothiazole-II, and

Figure 4:
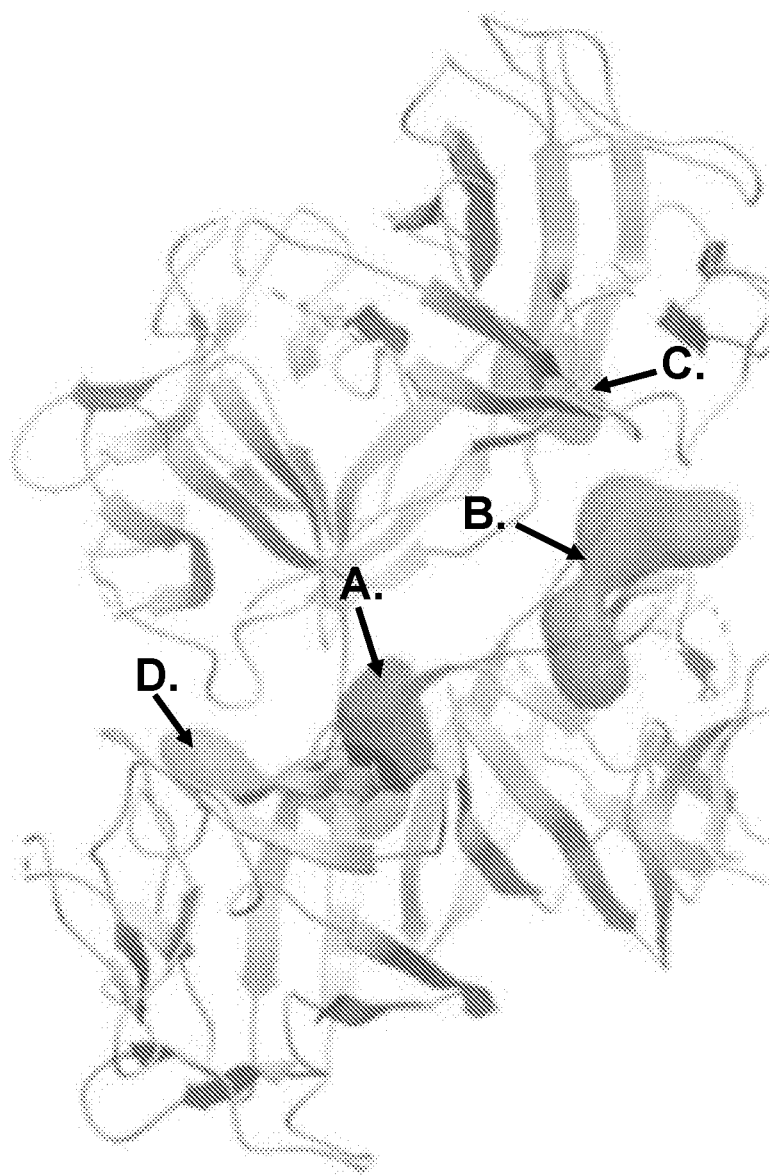
FIG. 4. A front view of four potential ligand binding pockets in human Fascin 1 (ribbon structure) are shown as grey-scale surfaces labeled A, B, C, and D.
Figure 5:
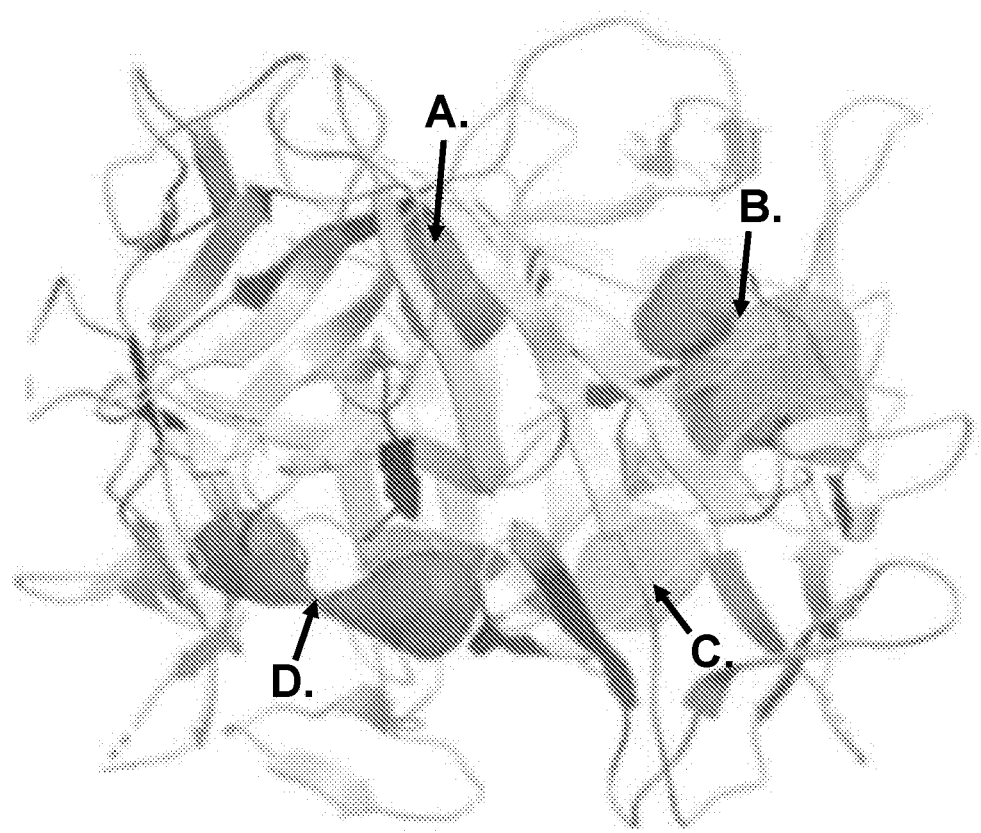
FIG. 5. A bottom view of the four potential ligand binding pockets in human Fascin 1 (ribbon structure) are shown as grey-scale surfaces labeled A, B, C, and D.
Figure 6:
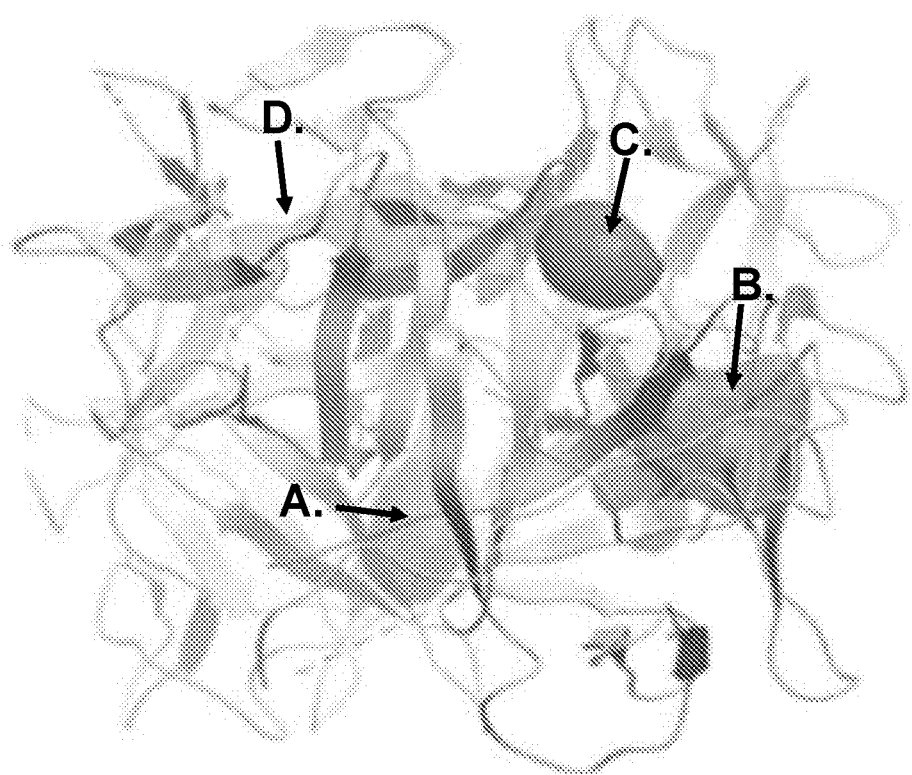
FIG. 6. A top view of the four potential ligand binding pockets in human Fascin 1 (ribbon structure) are shown as grey-scale surfaces labeled A, B, C, and D.
Figure 7:
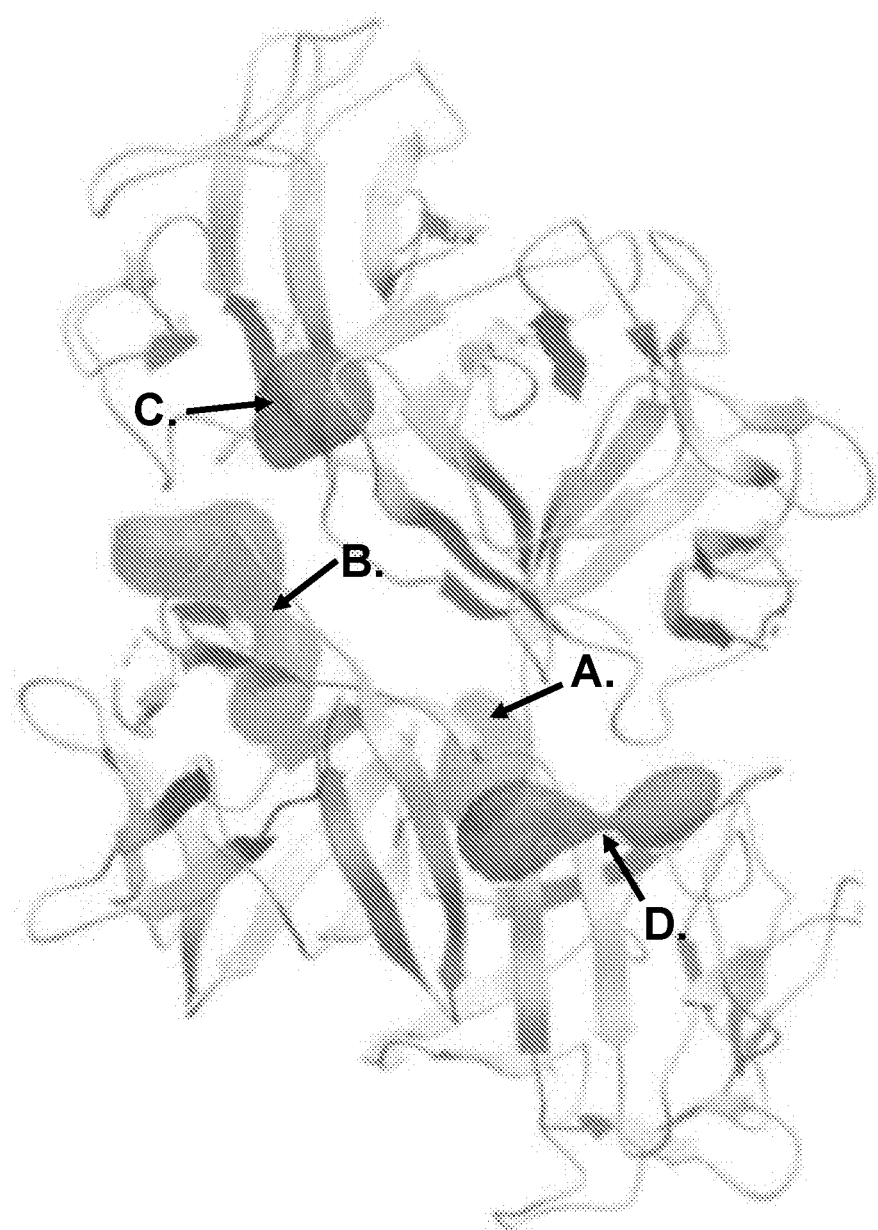
FIG. 7. A back view of the four potential ligand binding pockets in human Fascin 1 (ribbon structure) are shown as grey-scale surfaces labeled A, B, C, and D.

Benzothiazole-IIIA were docked to each of the four pockets shown in FIG. 4 using MolSoft's ICM-Docking software, Version 3.8-6a (Abagyan, R. & Totrov, M. *J. Mol. Biol.* 235, 983-1002 (1994)). The docking scores to each of the pockets are shown in Table 6. The lower the docking score the better the "compound-fascin binding pocket" interaction.

TABLE 6

Docking scores for the benzothiazole compounds to the four pockets, as shown in FIG. 4-7.

| | Head | | | Head + Tail | | |
|---|---|---|---|---|---|---|
| Pocket | Benzothiazole-I | Benzothiazole-II | Benzothiazole-IIIA | Benzothiazole-I | Benzothiazole-II | Benzothiazole-IIIA |
| A | −21 | −20 | −19 | −17 | −25 | −14 |
| B | −23 | −24 | −25 | −29 | −39 | −44 |
| C | −19 | −19 | −14 | −18 | −22 | −18 |
| D | −25 | −19 | −24 | −24 | −12 | −27 |

Figure 8:
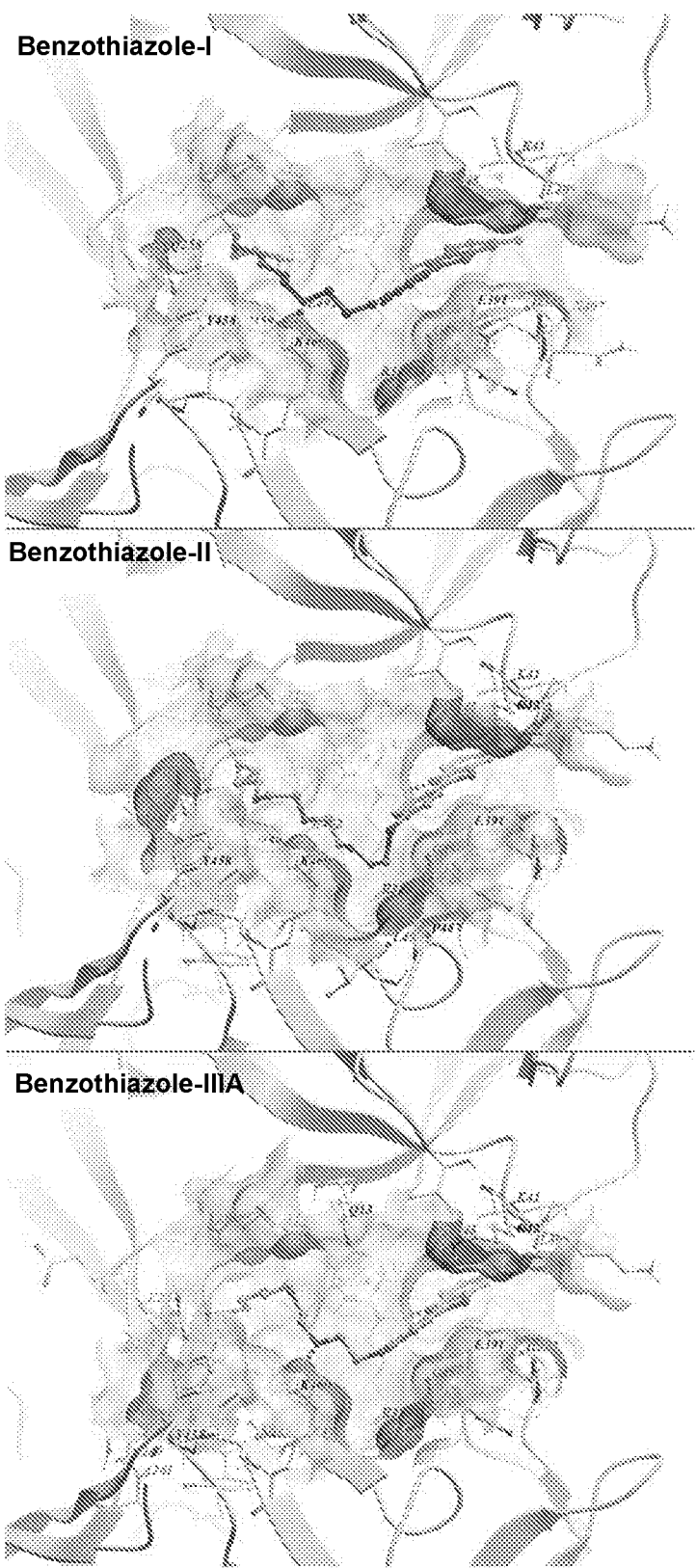
FIG. 8. The docked complexes of human Fascin 1 (ribbon structure) and Benzothiazole-I, Benzothiazole-II, and Benzothiazole-IIIA. The pocket surface incorporates aromatic lipophilic surfaces, non-aromatic other (mostly aliphatic) lipophilic surfaces, hydrogen bonding acceptor potentials, and hydrogen bond donor potentials.

Pocket B, which is located at the Actin Binding Site 1, resulted in the lowest docking score for almost every case, with the one exception being Benzothiazole-I (head), with a docking score of −25 for pocket D. Binding pocket B was investigated further in the other fascin crystal structures. It was noted that pocket B was close to the pentaethylene glycol binding site in PDB 3P53. The head group was docked to Pocket B in PDB 3P53, yielding significantly better docking scores using with the head group of each benzothiazole compound (Table 7). Using the docked head groups as the anchor point, the tail groups were then docked to produce the final energetically favorable compound poses, shown in FIG. 8.

TABLE 7

Docking scores for the head groups of the benzothiazole compounds to binding pocket B in PDB 3P53, which contains the pentaethylene glycol molecule.

| | Head | | |
|---|---|---|---|
| Pocket | Benzothiazole-I | Benzothiazole-II | Benzothiazole-IIIA |
| B | −54 | −57 | −57 |

Figure 9:
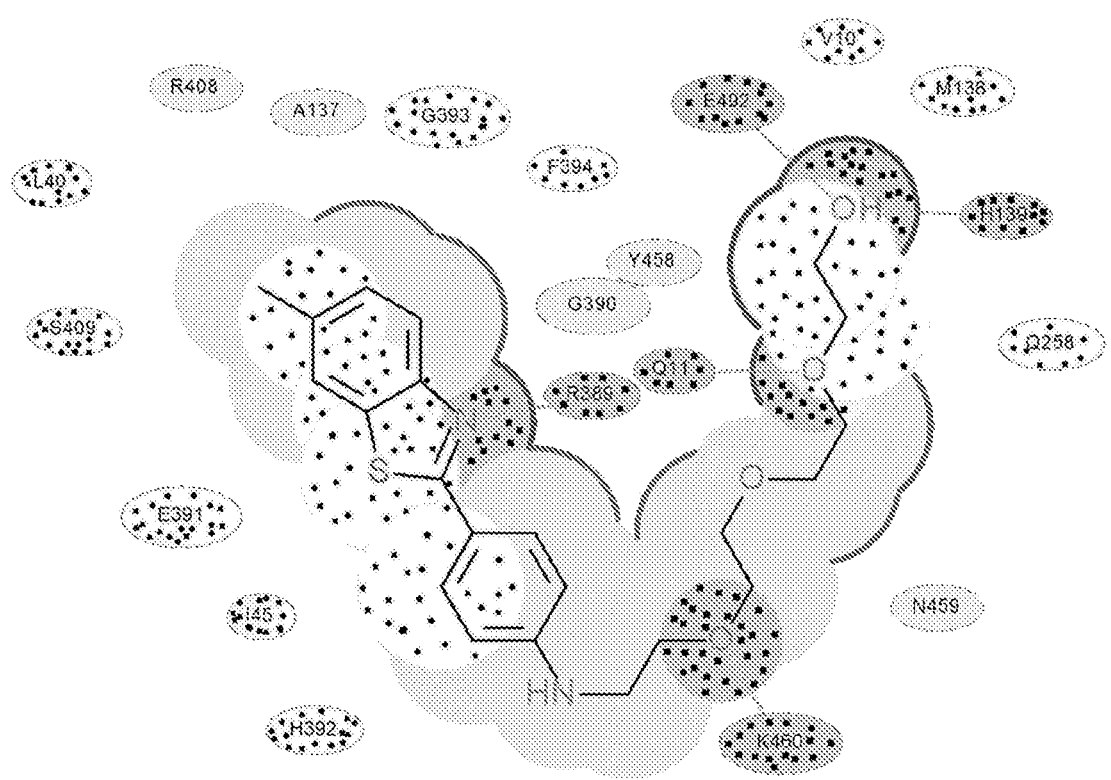
FIG. 9. A 2D interaction diagram of Benzothiazole-I and human Fascin 1 complex. Areas with black circles represent hydrophobic region. Shading with black squares represents hydrogen bond acceptor. Dashed lines represent hydrogen bonds. Solid grey parabolas represent accessible surface for large areas. Broken thick line around compound shape indicates accessible surface. Size of residue ellipse represents the strength of the contact. 2D distance between residue label and ligand represents proximity.

All three compounds, Benzothiazole-I, Benzothiazole-II, and Benzothiazole-IIIA, made a hydrogen bond from the nitrogen in the benzothiazole ring to ARG 389, and the first ethylene glycol makes a hydrogen bond with LYS 460. These interactions are depicted in FIG. 9, using Benzothiazole-I as an example.

In a similar docking experiment, the head+tail group of Benzothiazole-IIIB (FIG. 1) was docked to binding pocket B, with a docking score of −41. Based on this docking score of Benzothiazole-IIIB, and in view of the findings above, additional docking studies were performed with structural modifications of Benzothiazole-IIIB within Pocket B of Fascin. The docking scores of each modified Benzothiazole-IIIB are shown in Table 8 below.

TABLE 8

Docking scores for modified Benzothiazole-IIIB compounds to pocket B.

| Compound No. | Compound | Docking Score |
|---|---|---|
| 1 | 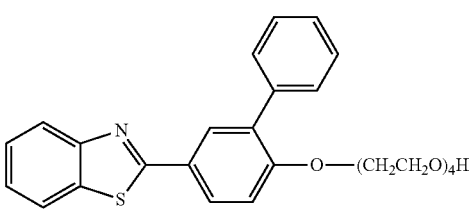 | −50.490913 |

TABLE 8-continued

Docking scores for modified Benzothiazole-IIIB compounds to pocket B.

| Compound No. | Compound | Docking Score |
| --- | --- | --- |
| 2 | benzothiazole-phenyl with allyl substituent and O—(CH$_2$CH$_2$O)$_4$H | −46.908085 |
| 3 | 4-hydroxybenzothiazole-phenyl-O—(CH$_2$CH$_2$O)$_4$H | −45.120392 |
| 4 | benzothiazole-phenyl with CH$_2$C(O)NH$_2$ substituent and O—(CH$_2$CH$_2$O)$_4$H | −44.67617 |
| 5 | benzothiazole-phenyl with vinyl substituent and O—(CH$_2$CH$_2$O)$_4$H | −44.280437 |
| 6 | benzothiazole-phenyl (2-vinyl, 4-O—(CH$_2$CH$_2$O)$_4$H) | −44.109577 |
| 7 | 7-vinylbenzothiazole-phenyl-O—(CH$_2$CH$_2$O)$_4$H | −43.765312 |
| 8 | benzothiazole-phenyl with CH$_2$CH$_2$OCH$_3$ substituent and O—(CH$_2$CH$_2$O)$_4$H | −43.597599 |
| 9 | benzothiazole-phenyl with COOH substituent and O—(CH$_2$CH$_2$O)$_4$H | −43.555912 |

TABLE 8-continued

Docking scores for modified Benzothiazole-IIIB compounds to pocket B.

| Compound No. | Compound | Docking Score |
| --- | --- | --- |
| 10 | Benzothiazole linked to phenyl with NHC(O)CH₃ and O—(CH₂CH₂O)₄H substituents | −43.526939 |
| 11 | Benzothiazole with 7-C(O)OCH₃ linked to phenyl-O—(CH₂CH₂O)₄H | −43.346741 |
| 12 | Benzothiazole with 7-NHC(O)CH₃ linked to phenyl-O—(CH₂CH₂O)₄H | −43.306965 |
| 13 | Benzothiazole with 7-C(O)CH₃ linked to phenyl-O—(CH₂CH₂O)₄H | −43.217476 |
| 14 | Benzothiazole linked to phenyl with OCF₃ and O—(CH₂CH₂O)₄H substituents | −43.11068 |
| 15 | Benzothiazole linked to phenyl with F and O—(CH₂CH₂O)₄H substituents | −43.002625 |
| 16 | Benzothiazole linked to phenyl with CH₃ and O—(CH₂CH₂O)₄H substituents | −42.988434 |
| 17 | Benzothiazole linked to phenyl with O-isopropyl and O—(CH₂CH₂O)₄H substituents | −42.96101 |

TABLE 8-continued

Docking scores for modified Benzothiazole-IIIB compounds to pocket B.

| Compound No. | Compound | Docking Score |
|---|---|---|
| 18 | benzothiazole-phenyl-O-(CH₂CH₂O)₄H with cyclopentyl | -42.910366 |
| 19 | benzothiazole-phenyl-O-(CH₂CH₂O)₄H with CH₂C(O)NH₂ | -42.905006 |
| 20 | benzothiazole-phenyl-O-(CH₂CH₂O)₄H with H₂NSO₂CH₂- | -42.829388 |
| 21 | benzothiazole-phenyl-O-(CH₂CH₂O)₄H with N(CH₃)₂ | -42.814205 |
| 22 | benzothiazole-phenyl-O-(CH₂CH₂O)₄H with OCF₃ | -42.798203 |
| 23 | benzothiazole-phenyl-O-(CH₂CH₂O)₄H with I | -42.727531 |
| 24 | benzothiazole-phenyl-O-(CH₂CH₂O)₄H with SO₂NH₂ | -42.689995 |
| 25 | benzothiazole-phenyl-O-(CH₂CH₂O)₄H with F | -42.594059 |

TABLE 8-continued

Docking scores for modified Benzothiazole-IIIB compounds to pocket B.

| Compound No. | Compound | Docking Score |
|---|---|---|
| 26 | benzothiazole with 7-N(CH3)2, 2-(4-O—(CH2CH2O)4H phenyl) | −42.542755 |
| 27 | benzothiazole with 6-OH, 2-(4-O—(CH2CH2O)4H phenyl) | −42.517101 |
| 28 | benzothiazole-2-(4-O—(CH2CH2O)4H, 3-SCH3 phenyl) | −42.508884 |
| 29 | benzothiazole-2-(4-O—(CH2CH2O)4H, 3-Br phenyl) | −42.496784 |
| 30 | benzothiazole with 7-F, 2-(4-O—(CH2CH2O)4H phenyl) | −42.47514 |
| 31 | benzothiazole-2-(4-O—(CH2CH2O)4H, 3-CH2C(O)NH2 phenyl) | −42.466572 |
| 32 | benzothiazole-2-(4-O—(CH2CH2O)4H, 3-CH3 phenyl) | −42.454689 |
| 33 | benzothiazole with 5-F, 2-(4-O—(CH2CH2O)4H phenyl) | −42.426392 |
| 34 | benzothiazole-2-(4-O—(CH2CH2O)4H, 3-N(CH3)2 phenyl) | −42.41114 |

TABLE 8-continued

Docking scores for modified Benzothiazole-IIIB compounds to pocket B.

| Compound No. | Compound | Docking Score |
| --- | --- | --- |
| 35 | Benzothiazole linked to phenyl with CF$_3$ group and O—(CH$_2$CH$_2$O)$_4$H substituent | −42.364777 |
| 36 | Benzothiazole linked to phenyl with OCH$_3$-ethyl group and O—(CH$_2$CH$_2$O)$_4$H substituent | −42.358681 |
| 37 | Benzothiazole linked to phenyl with F and O—(CH$_2$CH$_2$O)$_4$H substituent | −42.320164 |
| 38 | Benzothiazole linked to phenyl with NC and O—(CH$_2$CH$_2$O)$_4$H substituent | −42.307178 |

Example 4. Treating TBI Symptoms in an Adult Male with a Benzothiazole Compound

A 17-year old male patient without prior history of traumatic brain injury is experiencing disorientation, dizziness and a headache after having been unconscious for about 30 seconds as a result of being tackled during a football game. The patient's symptoms are observed and it is recognized that the head injury can be diagnosed as a TBI. Within about 30 minutes after receiving the head injury, a medical specialist at the scene confirms the patient's diagnosis of a moderate to mild traumatic brain injury using the Rivermead Post-Concussion Questionnaire, with a score of 32. The results of the RPQ assessment also showed that the patient was experiencing sensitivity to light, irritability, and aphasia. The patient is administered treatment for his traumatic brain injury.

The patient is treated with a benzothiazole compound, Benzothiazole-IIIB, administered in dosages of about 15 mg per kg once daily in the form of a capsule for several weeks. Thus, daily doses of Benzothiazole-IIIB, in the range of 1155 mg per day, over a period of about 14 to 35 days, will be used as an effective treatment for TBI.

During the course of his treatment, the patient's progress will be monitored by administering the RPQ assessment and will provide the barometer of the patient's overall improvement from treatment using the methods of the invention. The RPQ assessment will be given both before administration of Benzothiazole-IIIB (i.e., to diagnose the patient) and after administration of Benzothiazole-IIIB. The RPQ assessment will be carried out on days 1, 7, 14, 21, 28 and 35.

The patient will be given 1155 milligrams of Benzothiazole-IIIB once per day orally, over 35 days. By the seventh day of his treatment, the patient's Rivermead Post-Concussion Questionnaire scores are expected to decline from about 32 to about 24. This is indicative of a 25% improvement in the performance of one or more functional domains, specifically the physical, visual, cognitive-communication, and neurobehavioral domains. When the results of the RPQ are evaluated after the 35 day period, the patient will show an amelioration of a traumatic brain injury. Indeed, the patient is expected to improve in the performance of the effected domains by about 30% to 70% after the 35-day treatment.

This example illustrates how doses of benzothiazole compounds, in the range of about 1155 mg per day, given once daily over a relatively short period of time—about 35 days—are expected to reduce the symptoms of traumatic brain injury in a human patient.

Although the foregoing has been described in some detail by way of illustration and example for purposes of clarity and understanding, one of skill in the art will appreciate that certain changes and modifications can be practiced within the scope of the appended claims (e.g., substitutions of equivalents and other types of alterations to the compounds of this invention or salts, pharmaceutical compositions, derivatives, prodrugs, metabolites, tautomers or racemic mixtures thereof as set forth herein). Each aspect and embodiment described herein can also have included or incorporated therewith such variations or aspects as disclosed in regard to any or all of the other aspects and embodiments. In addition, each reference provided herein is incorporated by reference in its entirety to the same extent as if each reference was individually incorporated by reference.

What is claimed is:

1. A pharmaceutical composition comprising a compound according to Formula VII:

(VII)

$(R^1)_n$— [benzothiazole]—[phenyl with $(R^2)_p$]—O—$(CH_2CH_2O)_q$—H, or a pharmaceutically acceptable salt or solvate thereof, wherein:

subscripts n and p are each independently selected from 0, 1, or 2;

subscript q is an integer selected from 2, 3, and 5-8; and each $R^1$ and $R^2$ are independently selected from the group consisting of halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro, and one or more pharmaceutically acceptable excipients.

2. The pharmaceutical composition of claim 1, wherein:

subscript q is an integer selected from 3, 5, or 6;

$R^1$ is selected from the group consisting of halo, —OH, —CN, phenyl, —CHCH$_2$, —COCH$_3$, —COOCH$_3$, —CH$_2$SO$_2$NH$_2$, —NHCOCH$_3$, —N(CH$_3$)$_2$, —SCH$_3$, and —SO$_2$NH$_2$; and $R^2$ is selected from the group consisting of halo, —CH$_3$, —CH$_2$CH$_3$, cyclopentyl, —CF$_3$, —CN, —CHCH$_2$, —CH$_2$CHCH$_2$, phenyl, —CO$_2$H, —CH$_2$CO$_2$H, —CH$_2$CONH$_2$, —COOCH$_3$, —COCH$_3$, —(CH$_2$)$_2$OCH$_3$, —CONH$_2$, —CON(CH$_3$)$_2$, —CH$_2$SO$_2$N(CH$_3$)$_2$, —OCH$_3$, —OCF$_3$, —OCH(CH$_3$)$_2$, —N(CH$_3$)$_2$, —NHCOCH$_3$, —NO$_2$, —SCH$_3$, —SO$_2$CH$_3$, and —SO$_2$N(CH$_3$)$_2$.

3. The pharmaceutical composition of claim 1, wherein subscripts n and p are independently selected from 0 or 1, provided that subscripts n and p are not both 1.

4. The pharmaceutical composition of claim 1, wherein the compound is:

[benzothiazole]—[phenyl]—O—$(CH_2CH_2O)_6$H.

5. The pharmaceutical composition of claim 1, wherein:

$R^1$ is selected from the group consisting of halo, —CH$_3$, —OCH$_3$, phenyl, and —CN; and $R^2$ is selected from the group consisting of halo, —CH$_3$, —CF$_3$, —OCH$_3$, —OCF$_3$, CHCH$_2$, —CH$_2$CHCH$_2$, phenyl, and —NO$_2$.

6. The pharmaceutical composition of claim 1, wherein the compound of formula VII is represented by Formula VIIa:

(VIIa)

[substituted benzothiazole with $R^3, R^4, R^5, R^6$]—[phenyl with $R^7, R^8, R^9, R^{10}$]—O—$(CH_2CH_2O)_q$—H wherein:

subscript q is 5 or 6;

$R^3$, $R^4$, $R^5$, and $R^6$ are independently selected from the group consisting of hydrogen, halo, CH$_3$, and —OCH$_3$; and $R^7$, $R^8$, $R^9$ and $R^{10}$ are independently selected from the group consisting of hydrogen, halo, CH$_3$, —CF$_3$, —OCH$_3$, —OCF$_3$, phenyl, and —NO$_2$;

wherein at least six of $R^3$, $R^4$, $R^5$, $R^6$, $R^7$, $R^8$, $R^9$ and $R^{10}$ are hydrogen.

7. A method for increasing dendritic spine density of neurons comprising contacting the neurons with a pharmaceutical composition of claim 1 under conditions sufficient to increase dendritic spine density of neurons.

8. The method of claim 7, wherein the method is conducted subsequent to a patient receiving a traumatic brain injury.

9. A method for decreasing neurotoxicity of beta-amyloid peptides to neurons comprising contacting the beta-amyloid peptides with a pharmaceutical composition of claim 1 under conditions sufficient to decrease the neurotoxicity of the beta-amyloid peptides.

10. A method for reducing the symptoms of traumatic brain injury in a patient suffering from traumatic brain injury by administering the pharmaceutical composition of claim 1 under conditions sufficient to reduce the symptoms of traumatic brain injury.

11. The method of claim 10, wherein the method is conducted within about 0 to 72 hours of the traumatic brain injury.

12. The method of claim 10, wherein the reduction of the symptoms of trauma is measured by an improvement in the performance of one or more functional domains by at least 20% to 30% within about 7 days of treatment as compared to the performance of the one or more functional domains measured prior to treatment but after injury.

13. A method for increasing dendritic spine density of neurons comprising contacting the neurons with a compound according to Formula VII:

(VII)

$(R^1)_n$—[benzothiazole]—[phenyl with $(R^2)_p$]—O—$(CH_2CH_2O)_q$—H, or a pharmaceutically acceptable salt or solvate thereof, wherein:

subscripts n and p are each independently selected from 0, 1, or 2;

subscript q is an integer selected from 2, 3, and 5-8; and each $R^1$ and $R^2$ are independently selected from the group consisting of halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro, under conditions sufficient to increase dendritic spine density of neurons.

14. The method of claim 13, wherein the method is conducted subsequent to a patient receiving a traumatic brain injury.

15. A method for decreasing neurotoxicity of beta-amyloid peptides to neurons comprising contacting the beta-amyloid peptides with a compound according to Formula VII:

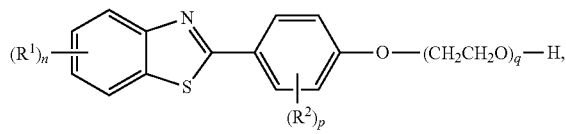

(VII)

or a pharmaceutically acceptable salt or solvate thereof, wherein:
subscripts n and p are each independently selected from 0, 1, or 2;
subscript q is an integer selected from 2, 3, and 5-8; and
each $R^1$ and $R^2$ are independently selected from the group consisting of halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro, under conditions sufficient to decrease the neurotoxicity of the beta-amyloid peptides.

16. A method for reducing the symptoms of traumatic brain injury in a patient suffering from traumatic brain injury by administering a compound according to Formula VII:

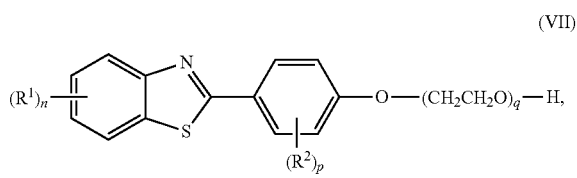

(VII)

or a pharmaceutically acceptable salt or solvate thereof, wherein:
subscripts n and p are each independently selected from 0, 1, or 2;
subscript q is an integer selected from 2, 3, and 5-8; and
each $R^1$ and $R^2$ are independently selected from the group consisting of halo, alkyl, substituted alkyl, alkenyl, substituted alkenyl, alkoxy, substituted alkoxy, acyl, acylamino, aminocarbonyl, aminosulfonyl, amino, substituted amino, aryl, substituted aryl, carboxyl, carboxyl esters, cyano, cycloalkyl, substituted cycloalkyl, heteroaryl, substituted heteroaryl, heterocyclyl, substituted heterocyclyl, hydroxyl, sulfonyl, substituted sulfonyl, thiol, thioalkyl, and nitro, under conditions sufficient to reduce the symptoms of traumatic brain injury.

17. The method of claim 16, wherein the method is conducted within about 0 to 72 hours of the traumatic brain injury.

18. The method of claim 16, wherein the reduction of the symptoms of trauma is measured by an improvement in the performance of one or more functional domains by at least 20% to 30% within about 7 days of treatment as compared to the performance of the one or more functional domains measured prior to treatment but after injury.

* * * * *

UNITED STATES PATENT AND TRADEMARK OFFICE
CERTIFICATE OF CORRECTION

| | | |
|---|---|---|
| PATENT NO. | : 12,391,659 B2 | Page 1 of 1 |
| APPLICATION NO. | : 17/392036 | |
| DATED | : August 19, 2025 | |
| INVENTOR(S) | : Stella Sarraf et al. | |

It is certified that error appears in the above-identified patent and that said Letters Patent is hereby corrected as shown below:

In the Claims

In Claim 5, Column 69, Line 63, please replace "$-CF_3$, $-OCH_3$, $-OCF_3$, $CHCH_2$, $-CH_2CHCH_2$," with -- $-CF_3$, $-OCH_3$, $-OCF_3$, $-CHCH_2$, $-CH_2CHCH_2$,--.

In Claim 6, Column 70, Line 16, please replace "hydrogen, halo, $CH_3$, and $-OCH_3$;" with --hydrogen, halo, $-CH_3$, and $-OCH_3$;--.

In Claim 6, Column 70, Lines 19-20, please replace "hydrogen, halo, $CH_3$, $-CF3$," with --hydrogen, halo, $-CH_3$, $-CF3$,--.

Signed and Sealed this
Twenty-eighth Day of October, 2025

John A. Squires
*Director of the United States Patent and Trademark Office*